US008336547B1

(12) United States Patent
Ritchie et al.

(10) Patent No.: US 8,336,547 B1
(45) Date of Patent: Dec. 25, 2012

(54) BREATHING MASK

(75) Inventors: Scott Craig Ritchie, San Diego, CA (US); Christopher Eames Woolley, San Marcos, CA (US)

(73) Assignee: Amron International, Inc., Vista, CA (US)

( * ) Notice: Subject to any disclaimer, the term of this patent is extended or adjusted under 35 U.S.C. 154(b) by 0 days.

(21) Appl. No.: 13/354,597

(22) Filed: Jan. 20, 2012

(51) Int. Cl.
*A62B 7/04* (2006.01)
*A62B 31/00* (2006.01)
*A62B 9/02* (2006.01)
*A62B 18/10* (2006.01)

(52) U.S. Cl. ......... 128/204.29; 128/204.18; 128/205.26; 128/201.282; 128/205.24; 128/200.24

(58) Field of Classification Search ............ 128/200.24, 128/201.27, 202.12, 203.29, 205.25, 205.26, 128/206.21; 600/21, 22
See application file for complete search history.

(56) References Cited

U.S. PATENT DOCUMENTS

| 2,473,518 | A | | 6/1949 | Garrard et al. |
| 2,551,653 | A | | 5/1951 | Wildhack |
| 3,099,987 | A | | 8/1963 | Bartlett |
| 3,329,158 | A | | 7/1967 | Geiszler |
| 3,375,839 | A | * | 4/1968 | Crenshaw ................ 137/81.1 |
| 3,783,891 | A | | 1/1974 | Christianson |
| 4,029,120 | A | | 6/1977 | Christianson |
| 4,041,978 | A | | 8/1977 | Leemann |
| 4,076,041 | A | | 2/1978 | Christianson |
| 4,095,592 | A | * | 6/1978 | Delphia ................. 128/204.21 |
| 4,147,176 | A | | 4/1979 | Christianson |
| 4,168,721 | A | | 9/1979 | Mueller, Jr. |
| 4,224,938 | A | | 9/1980 | Hilal |
| 4,226,257 | A | | 10/1980 | Trinkwalder |
| 4,266,538 | A | | 5/1981 | Ruchti |
| 4,378,011 | A | | 3/1983 | Warncke et al. |
| 4,449,524 | A | * | 5/1984 | Gray ..................... 128/202.27 |
| 4,498,471 | A | | 2/1985 | Kranz et al. |
| 4,503,852 | A | | 3/1985 | Christianson |
| 4,574,797 | A | | 3/1986 | Christianson |
| 4,616,645 | A | | 10/1986 | Pedersen et al. |
| 4,630,605 | A | | 12/1986 | Pasternack |
| 4,793,343 | A | * | 12/1988 | Cummins et al. ........ 128/204.17 |

(Continued)

OTHER PUBLICATIONS

Apeks Marine Equipment Ltd., http://www.apeks.co.uk/technical/technical_details.asp?Lan=ENG&Title=Cracking%20Resistance%20Control, Printed on Apr. 10, 2012.

(Continued)

*Primary Examiner* — Annette Dixon
(74) *Attorney, Agent, or Firm* — Knobbe Martens Olson & Bear LLP

(57) ABSTRACT

A breathing mask is disclosed, as well as a valve and a diverter that can be used within a breathing mask. The breathing mask can include a body, a respiratory interface, a balanced exhaust valve, and an inlet valve. The body can include an inlet and an exhaust. The respiratory interface can be configured to provide fluid communication between each of the inlet and the exhaust, and a user's respiratory system. The balanced exhaust valve can be configured to selectively flow fluid between the exhaust and the respiratory interface. The inlet valve can be configured to selectively flow fluid between the inlet and the respiratory interface. The valve can be a balanced exhaust valve with a fixed balance chamber. The diverter can include a tubular diverter body, a breathing port, an exhaust port, a demand port, and a diverter wall.

30 Claims, 10 Drawing Sheets

U.S. PATENT DOCUMENTS

| | | | |
|---|---|---|---|
| 4,850,346 A | | 7/1989 | Michel et al. |
| 4,862,884 A | | 9/1989 | Christianson |
| 4,966,196 A | | 10/1990 | Meyer |
| 5,035,238 A | | 7/1991 | Christianson |
| 5,092,325 A | * | 3/1992 | Ainscough ............... 128/201.27 |
| 5,251,618 A | | 10/1993 | Christianson |
| 5,259,375 A | | 11/1993 | Schuler |
| 5,501,213 A | | 3/1996 | Jackson |
| 5,503,140 A | | 4/1996 | Winefordner et al. |
| 5,549,107 A | | 8/1996 | Garraffe et al. |
| 5,690,097 A | * | 11/1997 | Howard et al. .......... 128/205.11 |
| 5,819,728 A | | 10/1998 | Ritchie |
| 5,871,011 A | * | 2/1999 | Howell et al. ............ 128/206.22 |
| 6,390,090 B1 | * | 5/2002 | Piper ........................ 128/203.28 |
| 7,793,656 B2 | | 9/2010 | Johnson |
| 2004/0154669 A1 | | 8/2004 | Semeia |
| 2005/0016537 A1 | | 1/2005 | Pedemonte |
| 2011/0036347 A1 | * | 2/2011 | Morgan et al. ........... 128/201.19 |

OTHER PUBLICATIONS

Life Support Engineering Ltd., Delta Bibs Mask Advertisement, Printed on Apr. 10, 2012.

\* cited by examiner

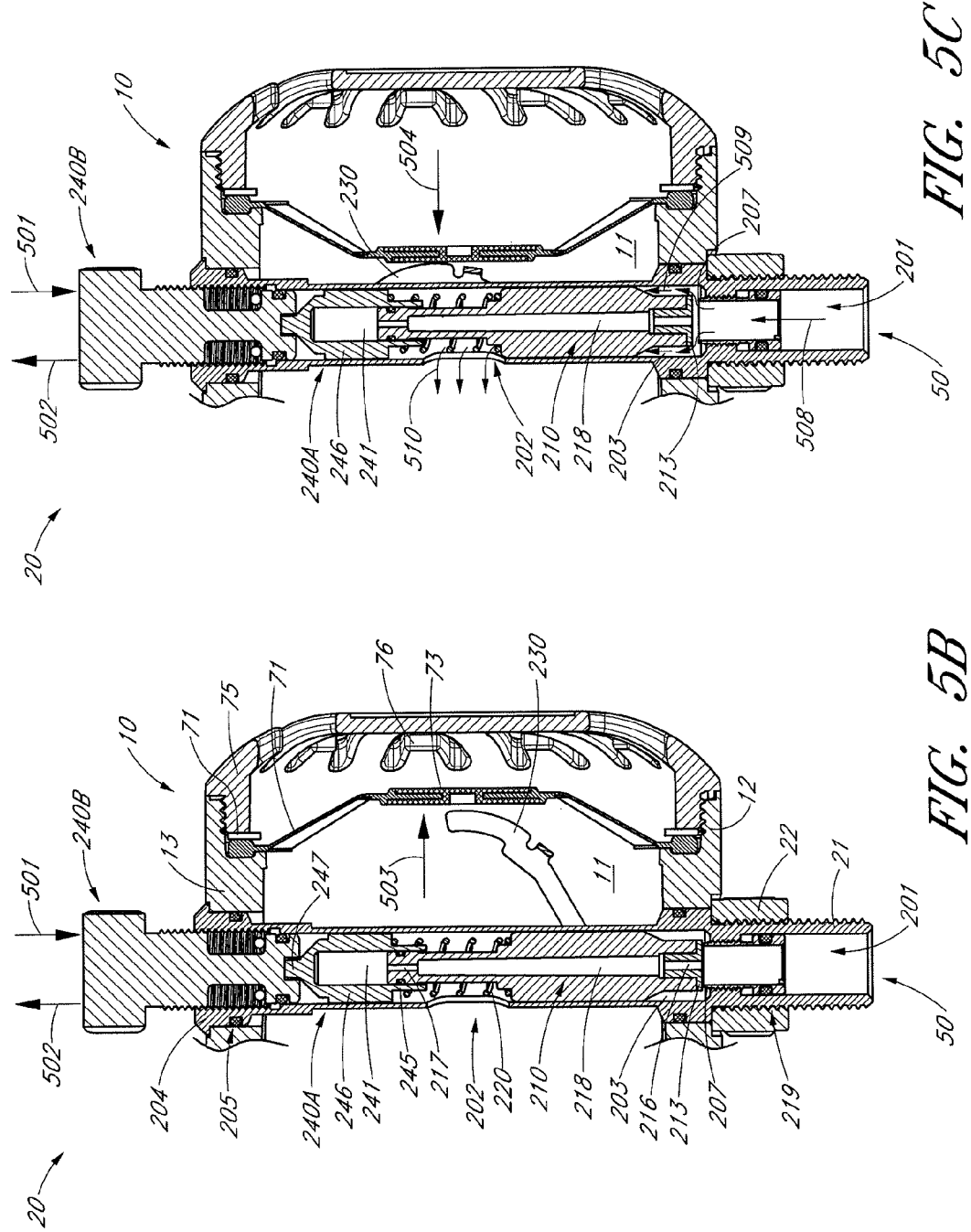

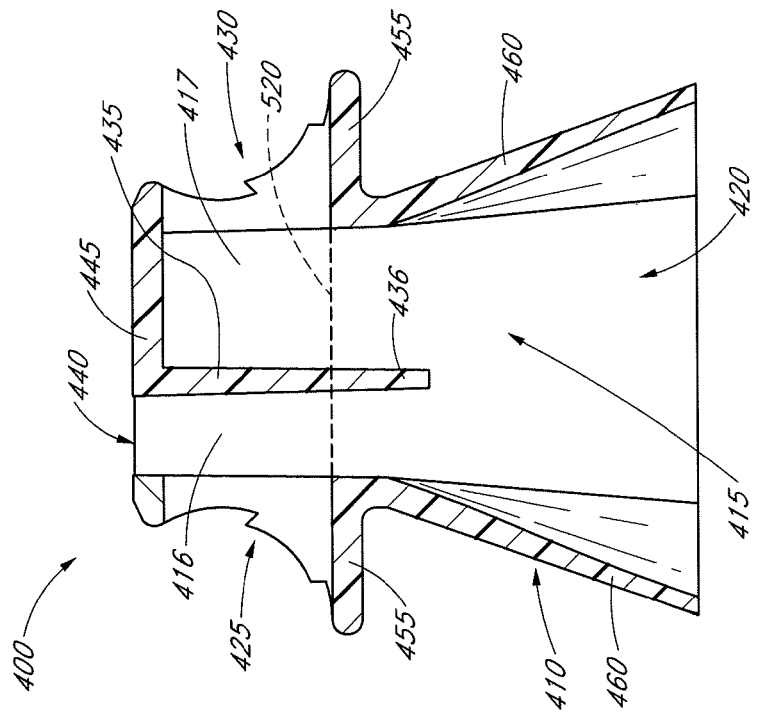
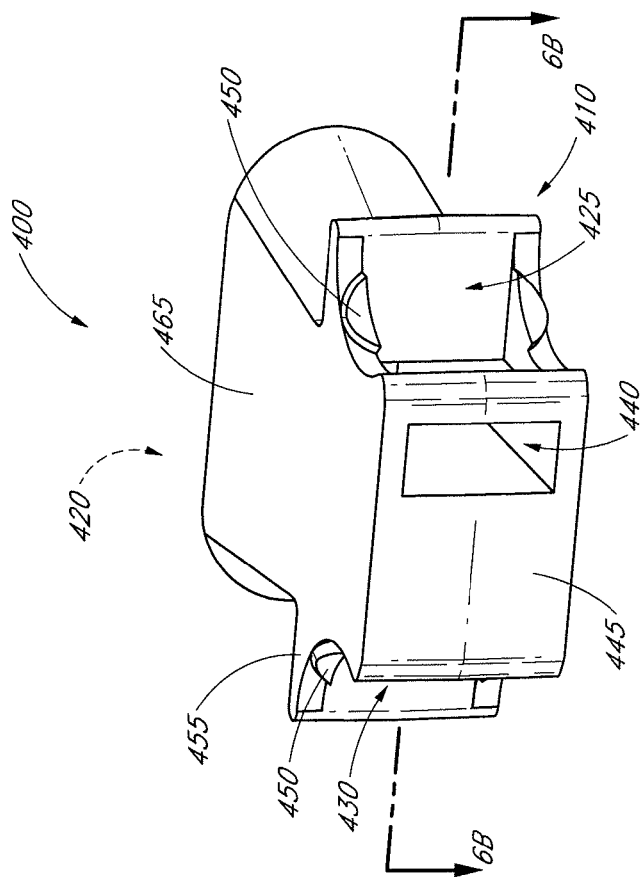
FIG. 6B
FIG. 6A

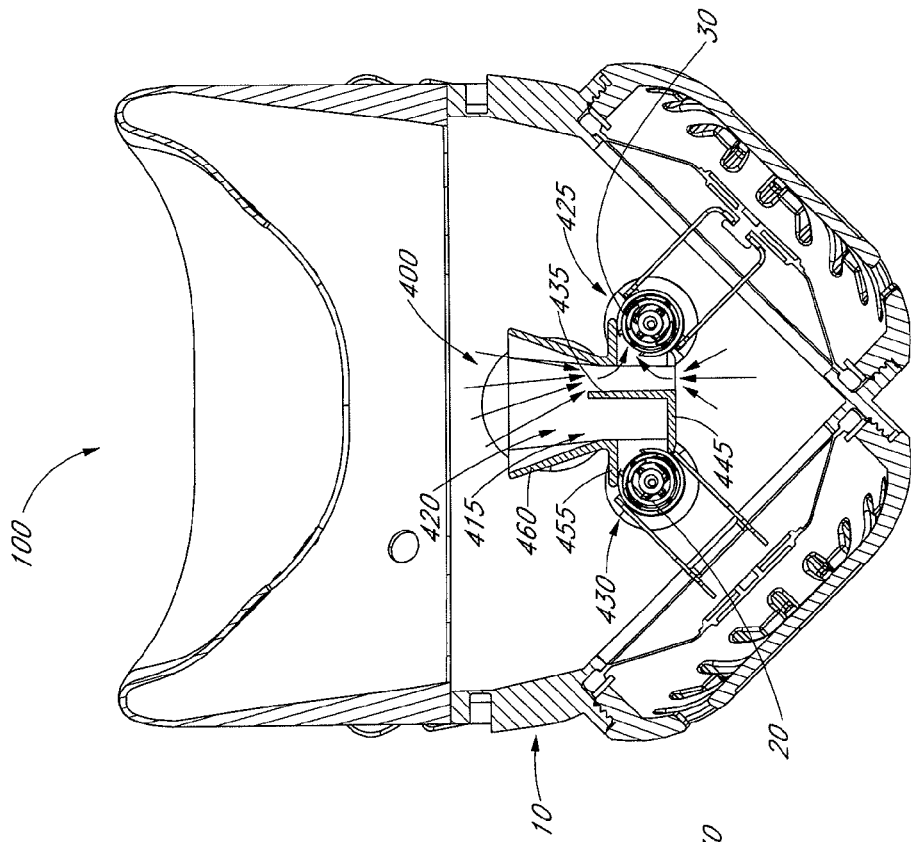
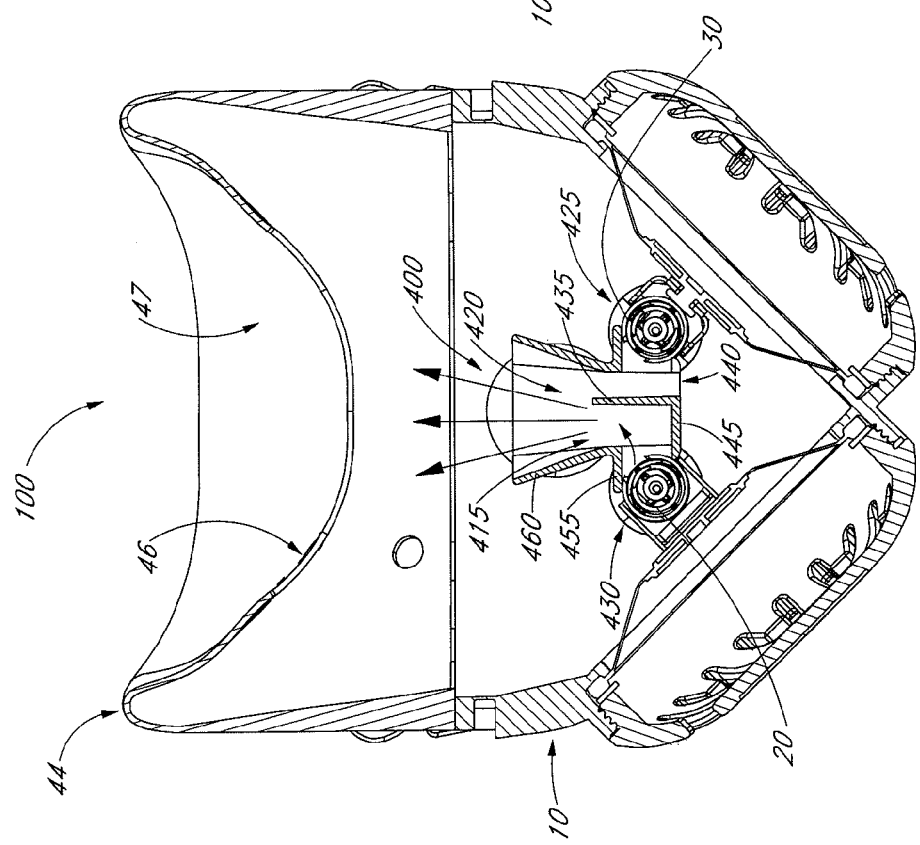

BREATHING MASK

BACKGROUND OF THE INVENTION

1. Field of the Development

This application relates to a breathing mask for fluid communication with a user's respiratory system. More particularly, this application relates to a balanced exhaust valve, a breathing mask implementing such an exhaust valve, and a diverter that can be employed within a breathing mask.

2. Description of the Related Art

Conventional breathing mask systems, such as diving masks, or masks for a hyperbaric, hypobaric or other atmospheric-controlled chamber, can be worn by a user to supply and exhaust breathing fluid such as air to and from a user's respiratory system. Such conventional masks may employ a valve to regulate the supply of such breathing fluid to the user. However, conventional masks, and the valves employed therein, may be limited in their range of environmental use, and may not be capable of reliably, accurately, and/or efficiently providing such breathing fluid to a user's respiratory system. Accordingly, there is a need for an improved breathing mask, and improved valves and other components that may be implemented with such a breathing mask.

SUMMARY

In accordance with one embodiment, a breathing mask for a hyperbaric chamber is provided. The breathing mask can include a housing, a pneumatically-balanced exhaust valve, a pneumatically-balanced demand valve, a first diaphragm, and a second diaphragm. The housing can be configured to form an inner volume. The housing can include an inlet configured to allow fluid flow into the inner volume, an exhaust configured to allow fluid flow from the inner volume, a posterior opening configured to provide fluid communication between the inner volume and a user's respiratory system, and first and second anterior openings extending through an anterior portion of the housing. The pneumatically-balanced exhaust valve can be configured to selectively flow fluid between the exhaust and the inner volume. The pneumatically-balanced demand valve can be configured to selectively flow fluid between the inlet and the inner volume. The first diaphragm can cover the first anterior opening. The second diaphragm can cover the second anterior opening. The first and second diaphragms can be configured to move in response to a change in pressure within the inner volume during inhalation and exhalation by a user. The first diaphragm can be mechanically linked to the exhaust valve such that the exhaust valve opens and closes in response to movement of the first diaphragm. The second diaphragm can be mechanically linked to the demand valve such that the demand valve opens and closes in response to movement of the second diaphragm. In an aspect of an embodiment, the housing further comprises a first aperture and a second aperture spaced from the inlet and the exhaust. In such an aspect, a portion of the demand valve and the exhaust valve, respectively, can be secured to the first and the second aperture. In another such an aspect of an embodiment, the first and second apertures can be positioned on a first portion of the housing, and the inlet and the exhaust can be positioned on a second, opposing portion of the housing. In such an aspect, the demand valve can extend across the inner volume between the first aperture and the inlet. The exhaust valve can extend across the inner volume between the second aperture and the exhaust. In such an aspect, the first portion of the housing can comprise a superior portion, and the second portion of the housing can comprise an inferior portion. In another aspect of an embodiment, one or more of the first and second diaphragms, the demand valve, and the exhaust valve can be substantially entirely enclosed within a perimeter formed around the inner volume of the housing. In another aspect of an embodiment, the first and second diaphragms, the demand valve, and the exhaust valve can be substantially entirely enclosed within the housing. In another aspect of an embodiment, a pair of covers can be configured to cover the first and second diaphragms. In another aspect of an embodiment, the demand valve and the exhaust valve can be configured to selectively flow fluid therethrough in a hyperbaric chamber simulating a diving depth of 450 m. In another aspect of an embodiment, the mask housing can comprise ABS and/or PC.

In accordance with another embodiment, a breathing mask can be provided. The breathing mask can include a body, a respiratory interface, a balanced exhaust valve, and an inlet valve. The body can comprise an inlet and an exhaust. The respiratory interface can be configured to provide fluid communication between each of the inlet and the exhaust, and a user's respiratory system. The balanced exhaust valve can be configured to selectively flow fluid between the exhaust and the respiratory interface. The inlet valve can be configured to selectively flow fluid between the inlet and the respiratory interface. In an aspect of an embodiment, the demand valve and the exhaust valve can be configured to selectively flow fluid therethrough in a hyperbaric chamber simulating a diving depth of 450 m. In another aspect of an embodiment, the mask housing can comprise ABS and/or PC.

In a further embodiment, a pneumatically-balanced exhaust valve can be provided. The pneumatically-balanced exhaust valve can include a valve body, a valve actuator, and a pneumatic balancer. The valve body can include a body inlet, a body exhaust, and a body channel extending between the body inlet and the body exhaust. The valve actuator can be positioned within the body channel and configured to be movable with respect to the valve body between an open and closed position, so as to selectively allow and restrict fluid flow between the body inlet and the body exhaust. The valve actuator can include a balance inlet, a balance outlet, and an inner balancing channel extending between the balance inlet and the balance outlet. The pneumatic balancer can include a balance chamber in fluid communication with the balance outlet. The balancer can be movably engaged with respect to the valve actuator body. In an aspect of an embodiment, the pneumatically-balanced exhaust valve can further comprise a spring configured to provide bias between the balancer and the valve actuator. In such an aspect, the spring can comprise a spring coefficient of less than or equal to 0.9 lbs/in. In another aspect of an embodiment, the pneumatically-balanced exhaust valve can further comprise a body valve seat portion configured to engage and disengage with a corresponding actuator valve seat portion when the valve actuator moves between a closed and opened position. In such an aspect, the body valve seat portion and the actuator valve seat portion can be adjustable with respect to each other, to adjust the amount of flow through the body channel. In another aspect of an embodiment, the valve actuator can comprise a plurality of fins extending from the valve actuator body such that the body channel extends at least partially longitudinally between the plurality of fins. In another aspect of an embodiment, the valve can be configured to open and close in a hyperbaric chamber simulating a diving depth of 450 m.

In a further embodiment, a breathing mask is provided. The breathing mask can include means for communicating fluid from within a mask body to a user's respiratory system. The breathing mask can further include means for selectively supplying fluid into the mask body. The breathing mask can further include means for selectively exhausting fluid from the mask body. The breathing mask can further include means for pneumatically balancing the selective supply means and the selective exhaust means. In an aspect of an embodiment, the means for balancing the selective supply means can comprise a floating means. In another aspect of an embodiment, the means for balancing the selective supply means can comprise a fixed means. In another aspect of an embodiment, the breathing mask can further comprise an activation means to activate the selective supply means and the selective exhaust means. In another aspect of an embodiment, the breathing mask can further comprise a diversion means for diverting fluid between the selective supply means and the selective exhaust means.

In a further embodiment, a method of using a breathing mask is provided. The method can include providing a breathing mask comprising a body, an inlet, an exhaust, and a respiratory interface. The method can further include selectively supplying fluid into the inlet of the mask body through an inlet valve, for inhalation by a user through the respiratory interface. The method can further include selectively exhausting fluid from the exhaust of the mask body through a pneumatically-balanced exhaust valve, for exhalation from a user through the respiratory interface. In an aspect of an embodiment, selectively supplying and selectively exhausting can comprise using the breathing mask in an environment that simulates a diving depth of 450 m.

In a further embodiment, a breathing mask diverter is provided. The diverter can include a tubular diverter body, a breathing port, an exhaust port, a demand port, and a diverter wall. The tubular diverter body can include an inner breathing channel. The breathing port can be configured to provide fluid communication between the inner breathing channel and a user's respiratory system. The exhaust port can be configured to engage the tubular diverter body with a breathing mask exhaust valve. The demand port can be configured to engage the tubular diverter body with a breathing mask demand valve. The diverter wall can extend within the tubular diverter body, wherein the diverter wall divides at least a portion of the breathing channel into an exhaust channel and a demand channel. The diverter wall can provide a barrier between the exhaust port and the demand port, so as to prevent the direct flow of fluid between the exhaust port and the demand port. In an aspect of an embodiment, a leading edge of the diverter wall can be positioned closer to the breathing port than a plane extending between a leading edge of the inlet port and a leading edge of the exhaust port.

BRIEF DESCRIPTION OF THE DRAWINGS

FIG. 5B is a side cross-sectional view of the demand valve of FIG. 5A and a portion of a breathing mask, showing the demand valve in a closed position.

FIG. 5C is a side cross-sectional view of the demand valve of FIG. 5A and a portion of a breathing mask, showing the demand valve in an open position.

FIG. 6A is a perspective view of an embodiment of a diverter for breathing mask.

FIG. 6B is a top cross-sectional view of the diverter of FIG. 6A taken along line 6B-6B of FIG. 6A.

FIG. 7A is a top cross-sectional view of the diverter of FIG. 6A assembled with a breathing mask and showing a demand valve of the breathing mask in an open position.

FIG. 7B is a top cross-sectional view of the diverter of FIG. 6A assembled with a breathing mask and showing an exhaust valve of the breathing mask in an open position.

DETAILED DESCRIPTION OF VARIOUS EMBODIMENTS

Although embodiments will be discussed below in terms of a breathing mask adapted for use in a hyperbaric chamber, and valves that can be implemented for use within such a mask, it will be understood that the inventions can be employed with other breathing mask applications.

There are many conventional designs of breathing masks and valves, such as those used for scuba diving. However, conventional diving masks and valves may not consistently and accurately open and close in response to the low vacuums and pressures inherent to a user's respiration, and may not even include a valve that can provide regulation and/or adjustment to the exhaust. Conventional designs may also not be rated for use within certain environments, such as the high pressure environment of a hyperbaric or saturation chamber designed to simulate a number of different diving depths. Conventional diving masks also have not provided a balanced demand valve and a balanced exhaust valve, which can improve the reliability and the pressure ranges in which a breathing mask can be used. Conventional diving masks may also require excessive effort on the part of a user's respiratory system, for example, to provide the cracking pressure to open or close a valve within the mask.

Disclosed herein are valves and breathing masks employing valves with improved reliability for a wider range of users and a wider range of environments. Some embodiments of these masks employ two separate diaphragm assemblies that activate an exhaust valve and an inlet valve, respectively. The inlet and/or exhaust valve can be balanced, to allow the valves to be more easily activated by a user's respiration, while still reliably closing the valves when desired. Some embodiments of these masks have provided unexpected results in testing. For example, in some embodiments, the amount of effort a user may exert with his or her respiratory system to open or close the valves within the masks described herein, may be less than 1.4 inches of water, or even as low as approximately 0.75 inches of water. Also disclosed herein is a router or diverter that can channel flow within a breathing mask to improve the reliability of a breathing mask, and the ability of the mask to efficiently supply fluid to a user.

The features, aspects and advantages of the present development will now be described with reference to the drawings of several embodiments, which are intended to be within the scope of the invention herein disclosed. These and other embodiments will become readily apparent to those skilled in the art from the following detailed description of the embodiments having reference to the attached figures, the invention not being limited to any particular embodiment(s) herein disclosed.

A Basic Device

Figure 1:
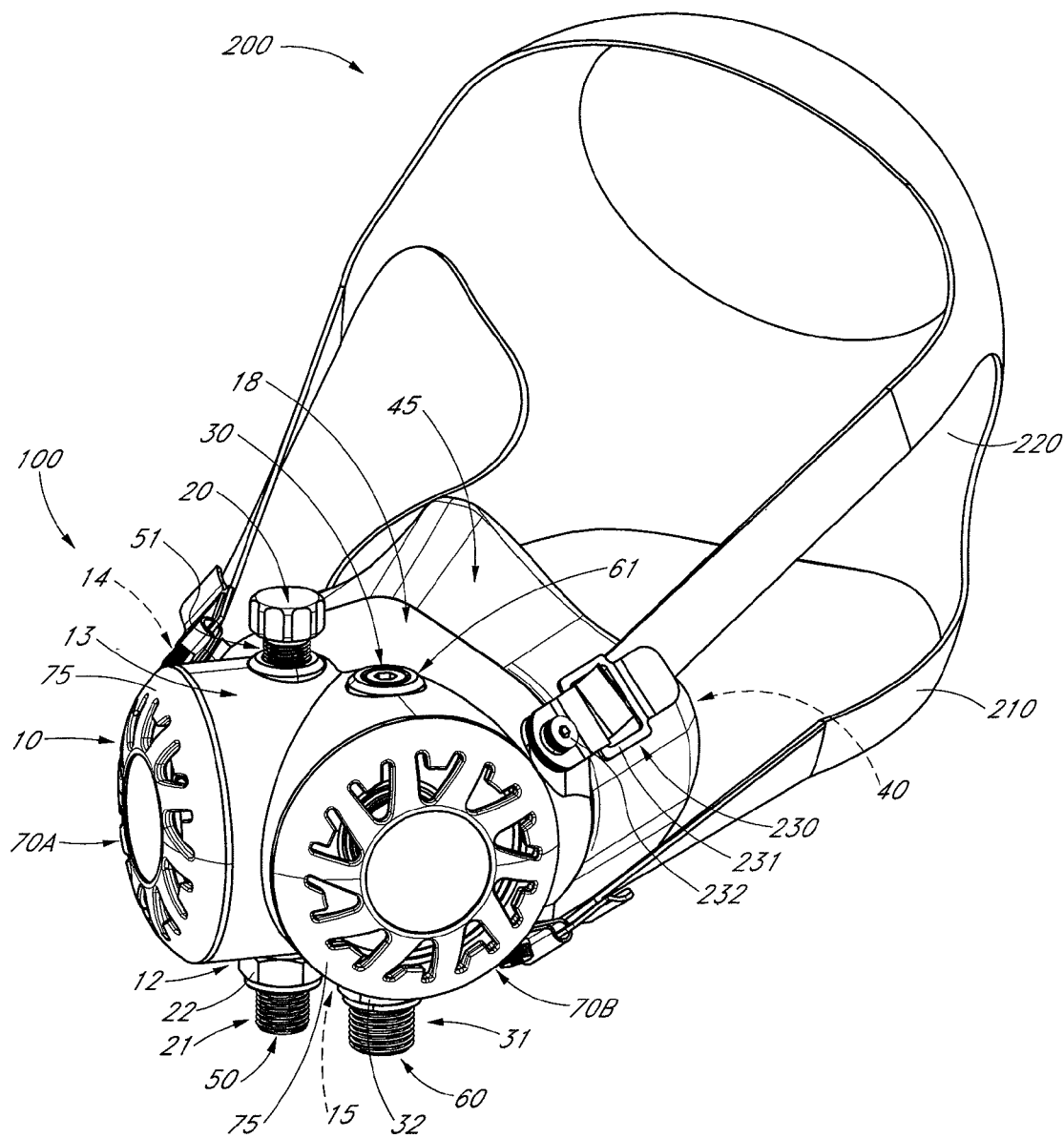
FIG. 1 is a perspective view of an embodiment of a novel breathing mask.
Figure 2:
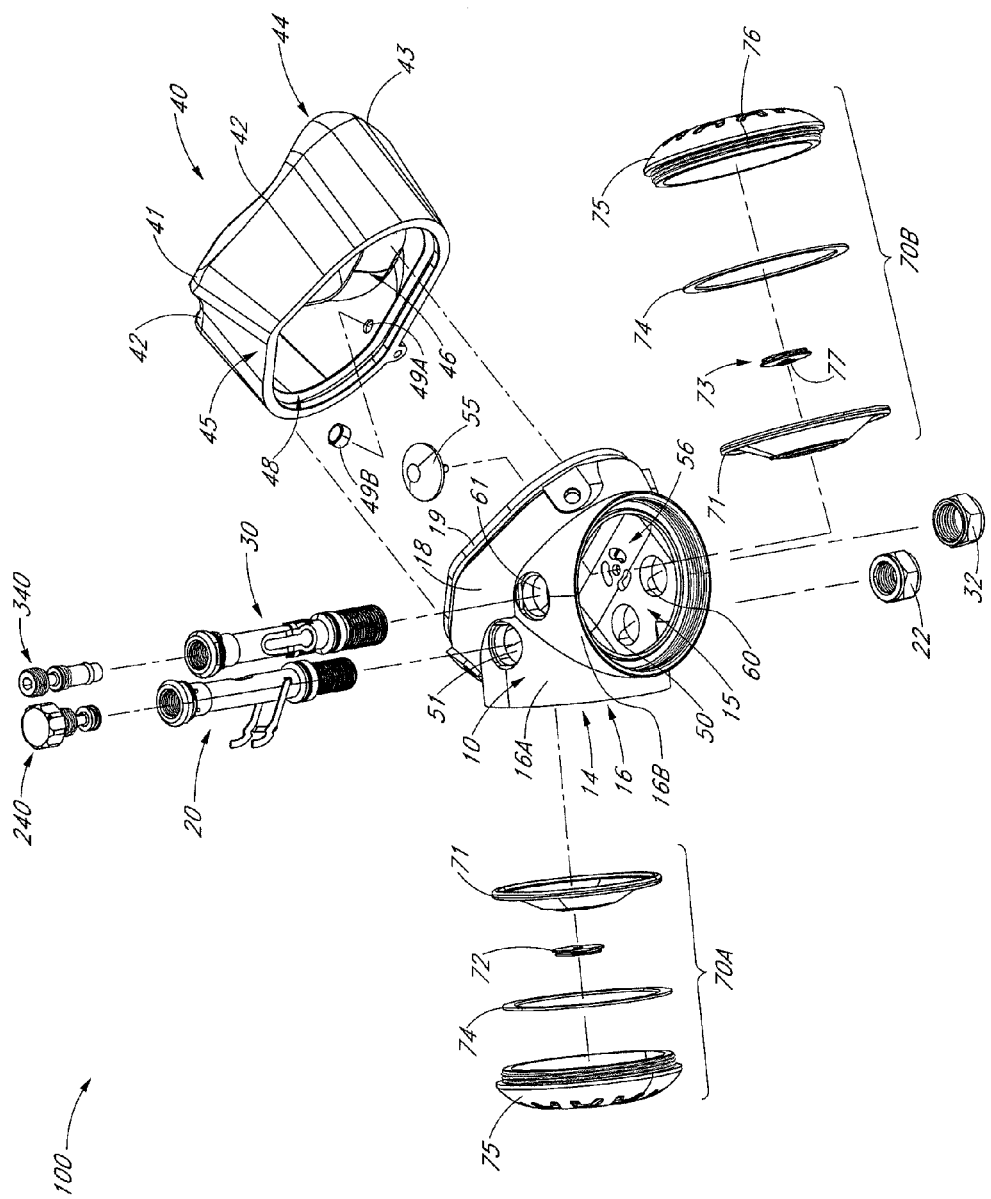
FIG. 2 is an exploded perspective view of the breathing mask of FIG. 1.
Figure 3:
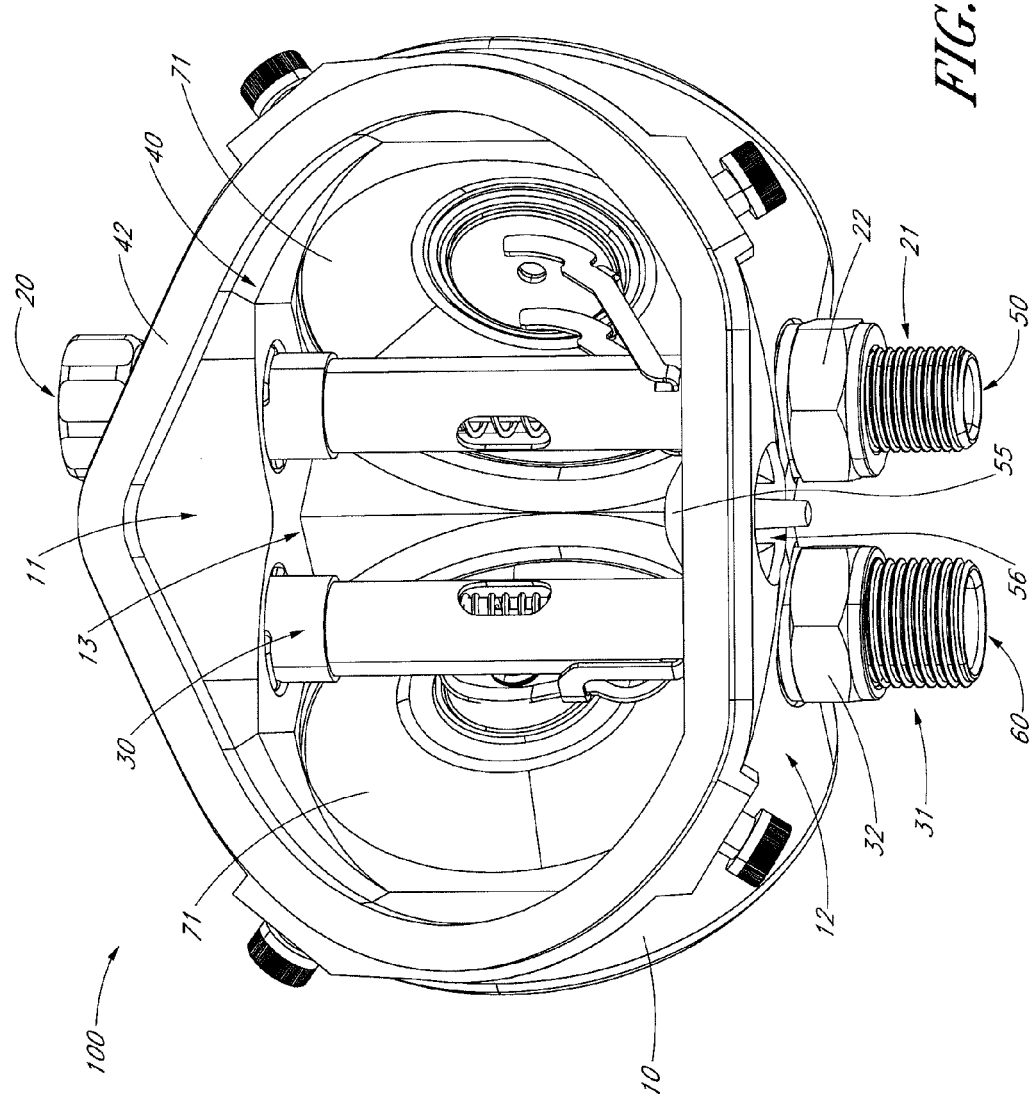
FIG. 3 is a rear view of the breathing mask shown in FIG. 2.

FIGS. 1 through 3 illustrate a breathing mask 100 according to an embodiment of the invention. The mask 100 generally includes a body or housing 10, an inlet or demand valve 20, an outlet or exhaust valve 30, and a respiratory interface 40. The respiratory interface 40 can be configured to provide fluid communication to a user's respiratory system from an inlet 50, and from a user's respiratory system to an exhaust 60. One or more fluid hoses, conduits, or other fluid-conveying structures can engage with inlet 50 and exhaust 60 to provide communication between mask 100 and a fluid supply and fluid exhaust, respectively (not shown). In some embodiments, the fluid exhaust can provide a negative pressure and flow from exhaust 60 and outlet valve 30, for example, in a range of −15 to −30 psig. In some embodiments, the fluid supply can provide a positive pressure of fluid into inlet 50 and inlet valve 20, for example in a range of 80 to 175 psig. It will be understood that "fluid" or "breathing fluid" as used herein can refer to any fluid that might be employed within breathing mask 100, and is not limited to a purely gaseous compound or mixture. Nor are these terms to be limited to a breathable fluid; for example, cleaning fluids that are not suitable for a user's respiratory system may be employed.

The inlet valve 20 can be configured to selectively flow fluid between the inlet 50 and the respiratory interface 40. The exhaust valve 30 can be configured to selectively flow fluid between the exhaust 60 and the respiratory interface 40. One or more activation elements, such as a diaphragm assembly, can be configured to selectively activate valves 20, 30. Preferably, a separate diaphragm assembly (diaphragm assemblies 70A and 70B), can be configured to selectively activate each of valves 20, 30, respectively. One or more, or in some embodiments, each of diaphragm assemblies 70A, 70B and valves 20, 30 can be substantially enclosed within the perimeter of mask housing 10, for a pleasing aesthetic, and to protect these components from damage by external forces. One or more of the valves 20, 30 can be balanced valves, or preferably, pneumatically-balanced valves, to allow for their activation with a reduced strain on a user's respiratory system, while still allowing for reliable activation, as described in further detail herein. In some preferred embodiments, the mask 100 is configured to facilitate its use in a high pressure or high vacuum environment, such as a decompression or hyperbaric chamber, at pressure ratings that simulate a diving depth of up to 450 meters (m), or in some embodiments, more than 450 m.

Referring to FIG. 1, an optional user mask support, such as a head support 200, can be provided to secure (e.g., removably secure) mask 100 to a portion of a user's face during use. Support 200 can be configured to wrap around or be secured to a portion of a user's head, neck, or shoulders, or other wearable articles worn by a user. The support 200 can comprise any of a number of configurations suitable for such purposes, and is shown with a number (four) of side straps 210, with a front or anterior portion connected to body 10, and a rear or posterior portion connected to a rear head strap 220. Support 200 can be attached to body 10 with any of a variety of attachment structures and methods known or described herein, including adhesive, snaps, buttons, hooks, tabs, buttons, a press fit, buckles, zippers, clasps, interference fit, snap fit, slots, grooves, screws, rivets, magnets, hook and loop systems (e.g., VELCRO®), and the like. For illustrative purposes only, support 200 is shown with straps 210 attached to buckles 230, which are attached to body 10 with fasteners 232. Straps 210 can include additional attachment structures on their ends, such as hook and loop systems, to prevent the loose ends of straps 210 from becoming entangled or otherwise inhibit use of the mask 100. For simplicity, head support 200 and one or more of its related components (straps 210, 220, buckles 230, fasteners 232) have been removed from the remaining Figures.

Body

With continued reference to FIGS. 1-3, the body 10 will be described in further detail. The body 10 can be any of a number of different shapes suitable to provide the selective flow of fluid through inlet 50 and outlet 60, the respiratory interface, and the user's respiratory system, as described in detail below. Preferably, body 10 can be configured to support valves 20, 30, to provide selective flow between the respiratory interface 40 and the inlet and outlet 50, 60. In some embodiments, body 10 can support one or more other components to provide additional functionality described herein. In the illustrated embodiment, body 10 comprises one or more portions that form a shell-like structure with an interior volume 11. It will be understood, however, that body 10 can include one or more substantially hollow, semi-solid, or solid portions, or combinations thereof. Body 10 can comprise one or more of a number of different rigid, semi-rigid, semi-flexible, or flexible materials suitable to provide the aforementioned functionality, such as metal or plastic. In some embodiments, body 10 is sufficiently thick and comprises a material sufficiently strong to withstand pressure in a hyperbaric chamber corresponding to a diving depth of up to 450 m. In an embodiment, body 10 comprises acrylonitrile butadiene styrene (ABS) and/or polycarbonate (PC).

The inlet 50 and outlet 60 can comprise any structure suitable to provide fluid communication between an external fluid supply and exhaust, and valves 20, 30. For example, inlet 50 and outlet 60 can include a fluid fitting mounted on and/or extending through a portion (e.g., sidewall) of body 10 configured to fluidly communicate with valves 20, 30. In the illustrated embodiment, inlet 50 and outlet 60 comprise one or more openings extending through body 10 into volume 11. It will be understood that inlet 50 and outlet 60 can be positioned at various portions of body 10, and are shown extending through an inferior (lower) portion 12 of body 10 for illustrative purposes only. Additionally, inlet 50 and outlet 60 can be positioned on the same or different portions of body 10, and can be positioned approximately adjacent to or spaced with respect to each other. For example, inlet 50 and outlet 60 can be positioned approximately adjacent to each other to support a manifolded design of valves 20, 30. Inlet 50 and outlet 60 can be positioned on the same portion (e.g., sidewall), opposed portions, parallel portions, or other portions of body 10 that are angled with respect to each other.

In some embodiments, inlet 50 and outlet 60 can provide support to valves 20, 30. For example, as described further below, valve 20 can include a valve inlet 21, and valve 30 can include a valve outlet 31, configured to extend through inlet 50 and outlet 60, and be secured to body 10 with an engagement element, such as nuts 22 and 32, respectively.

In some embodiments, body 10 can include additional optional engagement elements or structure to provide optional additional support to valves 20, 30. For example, apertures 51, 61 can extend through body 10, to secure an additional portion of valves 20, 30, respectively, to body 10. Apertures 51, 61 can be positioned in a variety of different ways, as described above for inlet 50 and outlet 60. In the illustrated embodiment, apertures 51, 61 extend through an upper (superior) portion 13 of body 10. Preferably, apertures 51, 61 are positioned on a portion of body 10 spaced from inlet 50 and outlet 60, to allow valves 20, 30 to at least partially extend across a portion of inner volume 11. In some embodiments, apertures 51, 61 are positioned on a portion of body 10 opposed from the portion of body 10 on which inlet 50 and outlet 60 are positioned. Such an embodiment can facilitate assembly of valves 20, 30 to body 10, by allowing insertion of valves 20, 30 through apertures 51, 61, through volume 11, and through apertures 50, 60. Valves 20, 30 can then be held in place by tightening nuts 22, 32. In some embodiments, these steps can be performed without any tools (by simply hand-tightening nuts 22, 32), and/or without needing to remove diaphragm assemblies 70A, 70B.

Extending valves 20, 30, through apertures 51, 61 can also allow a portion of valves 20, 30 to be accessed by a user. For example, valves 20, 30 can include one or more adjustment devices, such as pneumatic balancers 240, 340, respectively, as described further herein, to adjust the actuation and/or flow of valves 20, 30. Thus, when a portion of valves 20, 30 extends into, or through, apertures 51, 61, valves 20, 30, can be adjusted without their removal from mask 100, or removal of mask 100 from a user.

The body 10 can include additional support structure or engagement elements to support and facilitate the functionality of diaphragm assemblies 70A, 70B, described further herein. For example, openings 14, 15 can be configured to extend through a portion of body 10 and engage (e.g., receive) diaphragm assemblies 70A, 70B, respectively. Openings 14, 15 can include threads to engage with corresponding threads in assemblies 70A and 70B.

In the illustrated embodiment, openings 14, 15 are positioned to extend through an anterior (front) portion 16 of body 10. However, it will be understood that openings 14, 15 can be positioned in any of a number of different ways, such as those described above for inlet 50 and outlet 60. In the illustrated embodiment, anterior portion 16 comprises laterally-diverging portions 16A, 16B, that allow valves 20, 30, and diaphragms 70A, 70B to be positioned more closely to each other within body 10. Portions 16A, 16B can reduce the overall size of mask 100, while providing a desirable aesthetic. Portions 16A, 16B can be configured to include channels within volume 11 to direct air towards and away from diaphragm assemblies 70A, 70B, during user respiration.

An additional benefit of the aforementioned embodiments of body 10 is that one or more of diaphragm assemblies 70A, 70B, and/or valves 20, 30, or in some embodiments, all four of these components of mask 100, can be substantially entirely enclosed within the perimeter of body 10. "Substantially entirely enclosed" as used herein can be defined as the majority of a component being enclosed within the perimeter of body 10, while still allowing for adjustment, or removal of the components from the body 10. Thus, valves 20, 30 can include balancers 240, 340, and valve ports 21 and 31, and nuts 22 and 32, which may be outside of the perimeter of body 10, while valves 20, 30 are substantially entirely enclosed within the perimeter of body 10.

In some embodiments, mask 100 can include one or more safety features suitable to relieve vacuum and/or pressure being supplied to a user (e.g., within volume 11) that exceeds a certain amount, such as a pressure relief valve. For example, in the event that valve 30 fails in an open position, vacuum within mask 100 can provide an uncomfortable seal of mask 100 against a user's face, and may inhibit removal of mask 100 therefrom. Any suitable pressure relief device can be implemented; for example, an umbrella valve 55 can be implemented that relieves vacuum from mask 100 through apertures 56 when the vacuum within volume 11 exceeds a threshold. In an embodiment, umbrella valve 56 can be configured to relieve vacuum within mask 100 that exceeds approximately 25 in. of water, or 1 PSI.

Respiratory Interface

Continuing to refer to FIGS. 1-3, respiratory interface 40 can provide fluid communication between a user's respiratory system and other portions of mask 100, such as volume 11, inlet 50, exhaust 60, valve 20 and/or valve 30. In the illustrated embodiment, respiratory interface 40 comprises a channel extending through a face seal 45 (described further below), to provide fluid communication between valves 20, 30 and a user's respiratory system through the inner volume 11 of body 10.

Respiratory interface 40 can include any of a number of different shapes suitable to interface mask 100 with a user's respiratory system. Respiratory interface 40 can be configured as an opening or channel extending through a portion of body 10, such as a posterior (rear) portion 18. Respiratory interface 40 can be a separate or integral component with respect to body 10. In some embodiments, respiratory interface 40 can extend through a portion of body 10 and one or more intervening components, such as a shroud, face seal, or other structure that provides additional functionality, as will be discussed further below.

Respiratory interface 40 can comprise an elliptical, round, square, rectangular or other shape, and can include straight or curvilinear portions, or combinations thereof. In some embodiments, respiratory interface 40 can comprise a mouthpiece, conduit, tube, or other flow-conveying structure that provide fluid communication between valves 20, and a user's respiratory system. In some embodiments, respiratory interface 40 can be configured to at least partially conform (e.g., seal) to a user's face, and/or wrap at least partially, or preferably, completely, around a user's mouth and/or nose.

Face Seal

Referring to FIG. 2, interface 40 can be configured to extend through both a portion of body 10 (e.g., into volume 11; FIG. 3) and an intervening shroud-like structure or face seal 45. Face seal 45 can comprise a superior medial nose portion 41 with cheek portions 42 extending laterally from nose portion 41, and a mouth portion 43 that extends between cheek portions 42 and around a user's mouth.

Face seal 45 can comprise the same or different material than body 10, and/or can be separately or integrally formed with body 10. In a preferred embodiment, face seal 45 comprises a material that is more flexible than body 10, such as a flexible plastic, rubber, foam, and the like, to facilitate its conformance and/or engagement (e.g., sealing) with a portion of a user's face. Face seal 45 can be permanently or removably attached to body 10 using any of a number of attachment elements or methods known or described herein. In an embodiment, face seal 45 can comprise an anterior sealing portion 48 comprising a lip, groove, and/or other suitable components configured to engage and seal face seal 45 with a corresponding posterior sealing portion 19 of body 10 (FIG. 1). Preferably, face seal 45 can be removably attached to body 10, to allow for easy cleaning and maintenance.

In some embodiments, face seal 45 can include two or more sealing portions or surfaces with various profiles and/or positions with respect to each other and body 10. For example, and referring to both FIG. 2, face seal 45 can include a first outer perimeter seal 44, with an additional second inner perimeter seal 46, configured to conform and seal to various portions of a user's face. First seal 44, or portions thereof, can be positioned posterior to second seal 46, or portions thereof. Seal 44 can be configured to conform and seal around an outer portion of a user's face, including, for example, a user's chin and cheeks, whereas seal 46 can be configured to conform and seal around a portion of user's face closer to the user's mouth and nose or nostrils. Seals 44, 46 can include posterior-facing structure or surfaces, for example, to conform to an anterior-facing portion of a user's face, and/or can include other structure or surfaces facing in other directions, to conform to other portions of a user's face. For example, and referring to FIG. 7A, seal 46 can include a superior-facing portion 47 configured to engage at least partially with an inferior-facing portion of a user's chin, to act as a chin rest and/or seal.

Face seal 45 can include additional features to provide additional functionality to mask 100. For example, and referring to FIG. 1, face seal 45 can comprise a communication interface, such as a microphone cavity 49A and/or a microphone connector or interface 49B, configured to facilitate communication (e.g., wired or wireless communication) with a user of mask 100. It will be understood that a communication interface such as microphone cavity and connector 49A, 49B can be implemented within alternative or additional portions of mask 100, such as body 10, and/or head support 200. Additionally, the communication interface can include one or more components that facilitate one or two-way communication, and/or for communication between the user of the mask and one or more other systems or individuals.

Diaphragm Assemblies

Mask 100 can include one or more activation elements configured to selectively activate valves 20, 30, and to provide selective demand and exhaust of fluid to a user's respiratory system. In some embodiments, two activation elements are employed, with one provided to actuate each of valves 20, 30, to prevent reliability issues that have occurred in breathing masks that use only a single diaphragm. Preferably, the activation elements provide a fluid demand into mask 100 in response to a user's inhalation within respiration interface 40, and a fluid exhaust from mask 100 in response to a user's exhalation within respiration interface. Even more preferably, a separate activation element is used for each of valves 20, 30, to activate each valve independently in response to a user's inhalation and exhalation, respectively. In some embodiments, such activation elements can be mechanically linked to valves 20, 30, although it will be understood that any of a number of mechanical and/or electrical activation elements or systems suitable to selectively activate valves 20, 30 can be implemented within mask 100. An example of activation elements that can be employed within mask 100 are diaphragms 70A, 70B, as will be described presently.

Referring again to FIGS. 1-3, diaphragm assemblies 70A and 70B can comprise a flexible membrane or diaphragm 71 configured to cover openings 14, 15, and to flex and/or move in response to a user's respiration within mask 100. Diaphragm 71 can comprise any of a number of different cross-sectional shapes, such as a circle, ellipse, rectangle, or other regular or irregular shape. Diaphragm 71 can comprise substantially planar or non-planar surfaces in a quiescent or non-quiescent (flexed) state. In the illustrated embodiment, diaphragm 71 comprises an approximately round shape, with an optional convex surface on a first side which corresponds to a concave surface on the opposed side. Such concave/convex surface can provide a spring-like function that will tend to return diaphragms 71 to an initial position, or unflexed state. These opposed surfaces can be positioned in different orientations within assemblies 70A, 70B, and with respect to valves 20, 30. For example, diaphragm 71 can be positioned within assembly 70A with a concave surface facing valve 20 when in a quiescent state, and diaphragm 71 can be positioned within assembly 70B with a convex surface facing valve 30 when in a quiescent state, as described in detail below with reference to FIGS. 4A-5C. Diaphragm 71 can comprise any of a number of flexible materials suitable to cover and seal openings 14, 15, and flex in response to a user's respiration within mask 100, such as silicone.

Diaphragms 71 can be secured to body 10 to cover openings 14, 15 by using any of a number of attachment elements and methods known or described herein. In the illustrated embodiment, assemblies 70A, 70B include diaphragm covers 75 configured to secure diaphragms 71 to a portion of body 10 (e.g., portions 16A, 16B) and to protect and cover at least a portion of diaphragms 71. Covers 75 generally do not completely seal diaphragms 71 from the exterior of body 10, and generally include one or more apertures 76 to allow some flow through a portion of covers 75. Such flow in turn allows the diaphragms 71 to move and flex in response to a pressure differential across diaphragms 71, during a user's respiration in mask 100, as described in further detail below. It will be understood, however, that apertures 76 can extend through another portion of body 10 in addition or alternatively to covers 75, to provide such functionality to diaphragms 71.

Covers 75 can include threads that engage with corresponding threads on body 10. These engagement threads can be configured on the inner or outer perimeter (e.g., diameter) of covers 75 or portions 16A, 16B. In the illustrated embodiment, interlocking threads are positioned on the exterior of covers 75, and an interior of portions 16A, 16B of body 10, such that diaphragms 71 can be secured within portions 16A, 16B. Such embodiments can provide a pleasing aesthetic, flush, look to the assemblies 70A, 70B, and can prevent diaphragms 71 from being damaged. The threads can also allow a user to easily remove the covers 75 from body 10, for maintenance of diaphragms 71, or other portions of mask 100. In some embodiments, the threads can include a locking index tab, which can act as a stop or lock to hold covers 75 in a position that provides a desired compression and sealing to the diaphragms 71. In some embodiments, assemblies 70A, 70B can include an optional washer or spacer 74 configured to be positioned between diaphragms 71 and covers 75, to prevent wear on diaphragms 71 during removal and engagement of covers 75 on body 10.

Diaphragm assemblies 70A, 70B can be configured to engage diaphragms 71 with valves 20, 30 with any of a number of attachment elements or methods known or described herein. In the illustrated embodiment, assemblies 70A, 70B include valve engagement elements 72, 73 configured to attach to diaphragm 71, and engage with a movable portion of valves 20, 30. In the illustrated embodiment, valves 20, 30 include levers 230, 330, respectively, that can engage with valve engagement elements 72, 73, to selectively control flow through valves 20, 30 in response to movement of diaphragms 71. Valve engagement elements 72, 73 can be configured to provide additional rigidity and strength to diaphragms 71 at the point of their engagement with levers 230, 330. Valve engagement elements 72, 73 can be configured in any of a number of ways suitable to attach to diaphragms 71. In the illustrated embodiment, engagement elements 72, 73 include opposed walls and a stud-like member extending therebetween, wherein the walls are configured to secure to opposed sides of diaphragms 71 when the stud is extended through an opening in diaphragms 71.

Figure 4A:
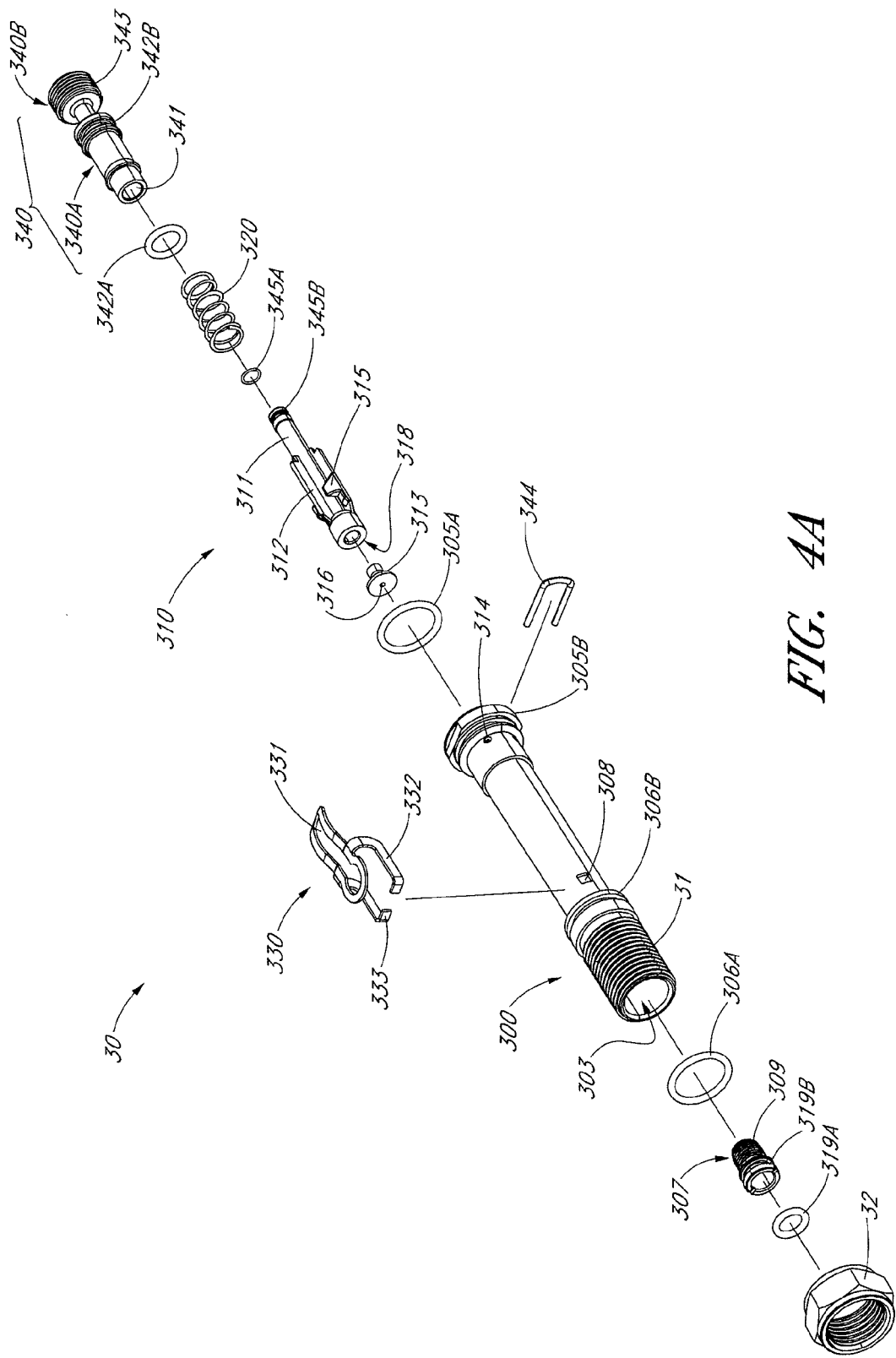
FIG. 4A is an exploded perspective view of an embodiment of a balanced exhaust valve for a breathing mask.
Figure 4C:
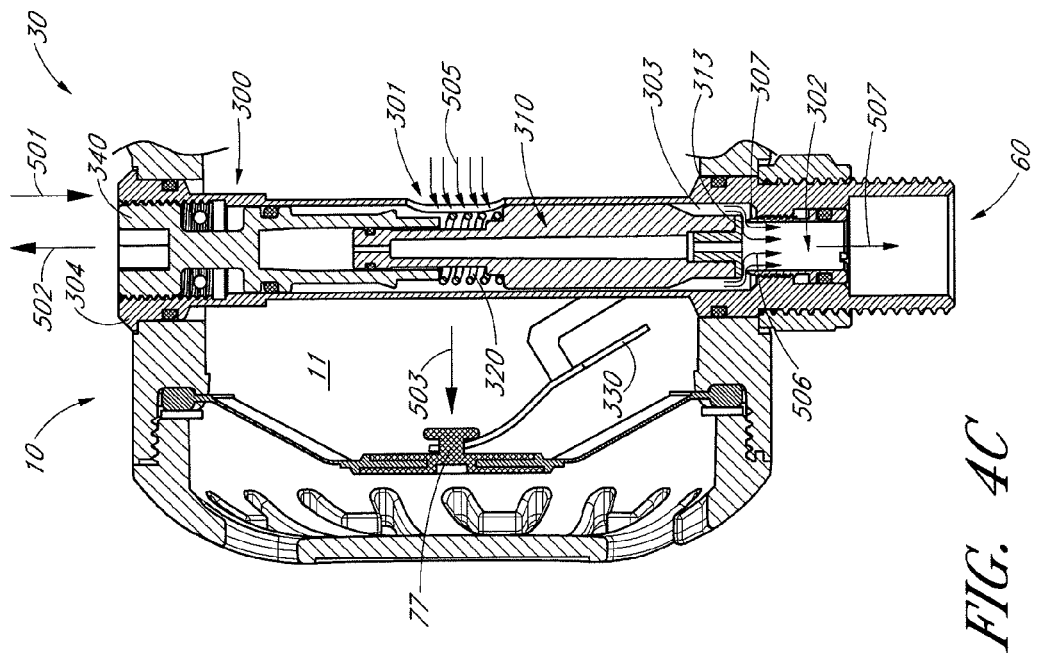
FIG. 4C is a side cross-sectional view of the exhaust valve of FIG. 4A and a portion of a breathing mask, showing the exhaust valve in an open position.
Figure 4B:
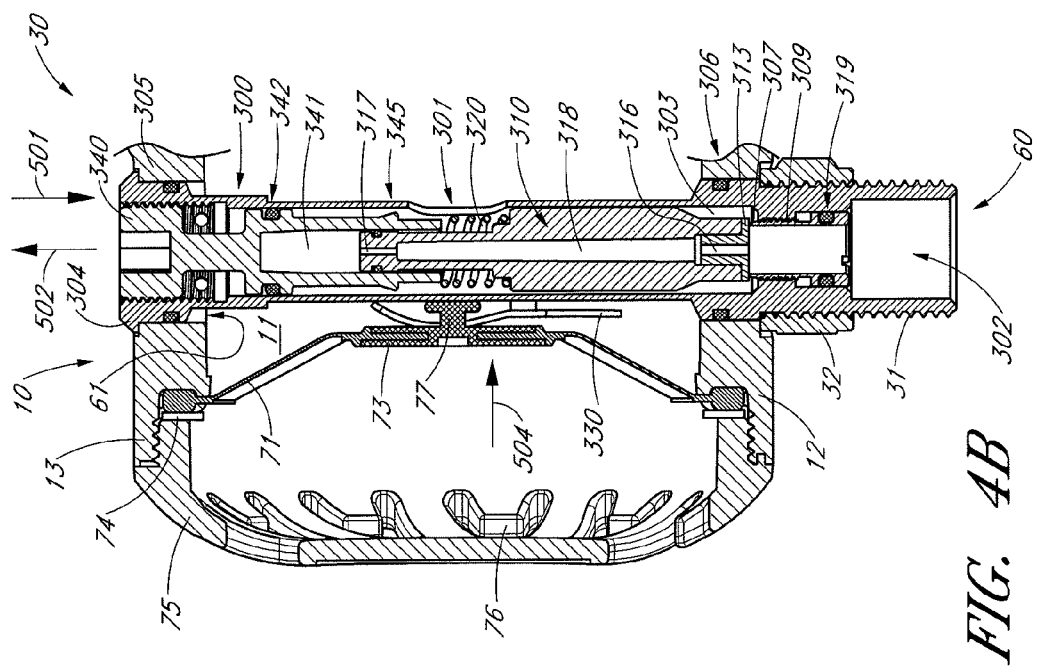
FIG. 4B is a side cross-sectional view of the exhaust valve of FIG. 4A and a portion of a breathing mask, showing the exhaust valve in a closed position.

Engagement elements 72, 73 can engage or link with a portion of valves 20, 30 without being completely attached thereto, for example, through a pressing contact, without additional structure, as described further below with respect to lever 230 and valve 20. In some embodiments, engagement elements 72, 73 can include additional optional structure to engage with levers 230, 330. For example, engagement element 73 can include a tab, tee, head, flange or other linkage 77 configured to engage with a slot 331 on lever 330 of valve 30 (FIGS. 4B and 4C). Additional details of the interrelationship and linkage between diaphragm assemblies 70A and 70B and valves 20, 30, is described further below with reference to FIGS. 4B-4C and 5B-5C.

Embodiments of valves 20, 30 will be described presently, beginning with exhaust valve 30.

Exhaust Valve

Valve 30 can move between a closed and opened position, to restrict and allow flow therethrough, and preferably, in response to a user's inhalation and exhalation, respectively. Referring to one or more of FIGS. 4A-4C, valve 30 can comprise a valve body 300 comprising a body inlet 301, a body exhaust 302, and a body channel 303 extending between the body inlet 301 and the body exhaust 302. When employed within mask 100, body inlet 301 can be in fluid communication with the respiratory interface 40, and body outlet 302 can be in fluid communication with exhaust 60. A valve actuator 310 can be positioned within the body channel 303. Valve actuator 310 can be configured to be movable with respect to the valve body 300 between an open and closed position, so as to selectively restrict (FIG. 4B) and allow (FIG. 4C) fluid flow between the body inlet 301 and the body exhaust 302. Valve 30 can include a spring 320 to provide bias between valve body 300 and valve actuator 310, to bias actuator 310 towards a closed position. The bias in spring 320 can prevent the valve 30 from sticking or failing in an open position during use without vacuum on exhaust 60, or during shipping of mask 100. In embodiments in which a vacuum or negative pressure is applied to exhaust 60, both the vacuum and spring 320 can provide a bias against valve actuator 310 towards a closed position. In some embodiments, the bias caused by the vacuum, and/or the balancing features described further herein with respect to exhaust valve 30, can allow spring 320 to be a relatively low spring constant, for example, approximately 0.9 lbs/in., or less than or equal to 0.9 lbs/in., while still providing consistent actuation of valve 30.

Valve body 300 can comprise a tubular structure configured to form channel 303 and receive valve actuator 310. It will be understood that valve body 300 can comprise any structure suitable to movably engage with the valve actuator 310 and form channel 303, with, for example, a square, rectangular, circular, or elliptical cross section, and/or with one or more hollow portions, grooves and the like. In some embodiments, valve body 300 can be sized and shaped to allow insertion of valve 30 into mask body 10 in a first direction (indicated by arrow 501) and removal from mask body 10 in a second, opposed direction (indicated by arrow 502) through aperture 61 and exhaust 60 in body 10, without disassembly of valve 30 prior to or during said insertion and removal (see also FIG. 2). Valve body 300 can also be configured such that valve 30 spans between or across two portions of body 10, such as lower and upper portions 12, 13 within volume 11, when employed within mask 100. Valve body 300 can comprise a material with sufficient strength and rigidity to support its use in a hyperbaric chamber, such as metal, plastic, or combinations thereof. In an embodiment, valve body 300 comprises Stainless Steel, such as 316SS, ABS, PC, Viton, and/or combinations thereof.

Body inlet 301 and exhaust 302 can be positioned along various positions of body 300, and can comprise any of a number of different shapes and sizes that provide the fluid communication between body channel 303. In the illustrated embodiment, body inlet 301 is approximately centered along body channel 303, to guide flow and reduce turbulence into inlet 301 when valve 30 is employed within body 10.

Valve 30 can include additional structure to facilitate its sealing, engagement, and support with respect to body 10 of mask 100. For example, as described above, valve body 300 can include threads 31 configured to secure valve 30 to body 10 with nut 32 when valve 30 is inserted into aperture 61 and exhaust 60. Valve 30 can include a stop or other suitable structure, such as a flange or head 304 extending from a portion of valve body 300, to prevent over-insertion of valve 30 into body 10.

Valve 30 can comprise one or more seals configured to seal valve 30 and body 10 with respect to each other at their point of interface, to prevent the likelihood of fluid leaking from body 10. For example, a first seal 305 can be positioned between a portion of valve body 300 (e.g., an outer perimeter or diameter at its superior end) and aperture 61. A second seal 306 can provide a seal between a portion of valve body 300 (e.g., an outer perimeter or diameter at its inferior end) and exhaust 60 of body 10. Seals 305, 306 can comprise any suitable sealing system known or described herein, such as a lip seal, face seal, o-ring and the like. In the illustrated embodiment, seals 305, 306 comprise an o-ring 305A, 306A configured to be captured by grooves 305B, 306B, respectively, extending into a portion of valve 30 (e.g., an outer surface of body 300), to capture o-rings 305A, 306A. It will be understood that one or more grooves can extend into a portion of body 10 (e.g., an inner surface of aperture 61 or exhaust 60), to capture an o-ring and provide similar sealing function.

Valve actuator 310 can comprise any configuration suitable to movably engage with valve body 300 between an open and closed position, and selectively control fluid flow between the body inlet 301 and the body exhaust 302. In some embodiments, valve actuator 310 can comprise a valve actuator body 311 configured to be received by body 300 within body channel 303. Valve actuator body 311 and body 300 can be configured and positioned such that fluid can flow within body channel 303 between an inner portion of body 300 and an outer portion of valve actuator body 311. Valve actuator 310 can comprise any of a number of materials suitable for the function described herein, such as metal, or a plastic such as acetone or delrin. In a preferred embodiment, an ABS carbonate blend can be used, for example, to prevent outgassing, and to allow its use in a military application.

In some embodiments, valve actuator 310 can include one or more optional support members suitable to position and provide support (e.g., radial positioning and support) between valve actuator 310 and valve body 300. In the illustrated embodiment, such support members comprise ribs 312 that extend outwardly from body 311. Ribs 312, or other suitable support members, can be spaced around the perimeter of body 311 with respect to each other, to allow flow within body channel 303, between one or more adjacent support members, and between the body inlet and exhaust 301 and 302. The ribs or support members can be straight, parallel, and/or evenly spaced with respect to each other about valve actuator body 311, as shown, or can be curvilinear, non-parallel, or unevenly spaced with respect to each other.

Valve actuator 310 can provide selective flow through valve 30 in a number of different ways. In some embodiments, an actuator valve seat portion 313 can be configured to selectively close or seal (FIG. 4B) and open or unseal (FIG. 4C) actuator 310 with respect to a corresponding body valve seat portion 307, in response to movement of actuator 310 and body 300 with respect to each other. Valve seats 313, 307 can comprise any of a number of different configurations and orientations, and are shown with opposed, substantially planar, longitudinally-facing surfaces for illustrative purposes only. Valve seats 313, 307 can be integrally formed with valve actuator 310 and body 300, respectively, or can be formed as part of one or more intermediate components that can be inserted and/or attached (e.g., removably) to the remainder of actuator 310 and body 300. In some embodiments, the positioning of seats 313, 307 can be adjustable with respect to each other, as described further below.

Referring to FIGS. 4B and 4C, actuator 310 can be linked (e.g., mechanically) to diaphragm 71 to provide the aforementioned movement between actuator 310 and body 300. As used herein, "linked" does not necessarily mean directly linked, and can mean directly linked, or linked through one or more intermediate components. Additionally, unless otherwise specified, "linked" can mean sufficiently engaged such that motion can be transferred in one or more directions. An activation member, shown as lever 330 for illustrative purposes, can attach to diaphragm 71 and valve actuator 310. Lever 330 can include a slot 331 or other suitable attachment element that engages (e.g., movably or slidably) with the head 77 of engagement element 73 of diaphragm assembly 70B. Lever 330 can include lever arms 332 with lever tabs 333 configured to engage with a portion of valve actuator 310, such as actuator tabs 315 (FIG. 4A). Lever tabs 333 can engage with actuator tabs 315 when they are extended through apertures 308 in valve body 300 (see FIG. 4A).

When valve 30 is in an at-rest position, or when a user is inhaling, diaphragm 71 is held in the position shown in FIG. 4B. In such a position, lever 330 is engaged with actuator tabs 315 in a position such that actuator 310 and valve 30 are closed, restricting flow between seats 307 and 313, and between inlet 301 and outlet 302 through channel 303.

Referring to FIG. 4C, when a user exhales, pressure on diaphragm 71 causes it to move or flex outwardly, in the direction shown by arrows 503. In response, head 77 causes lever 330 to move, which in turn causes lever tabs 333 to engage with and move actuator tabs 315. This in turn causes actuator 310 to move from a closed to an open position (see also FIG. 4A). Once valve 30 opens, fluid (e.g., a user's breath) can flow through inlet 301 (arrows 505; FIG. 4C), through channel 303, between seats 307 and 313 (arrows 506), and out the exhaust 302 (arrow 507). Upon a user's subsequent inhalation, the valve 30 will return to the closed configuration shown in FIG. 4B, with the diaphragm 71 moving inwardly to closed position, as indicated by arrow 504.

Valve 30 can comprise a balanced exhaust valve, to provide improved reliability for a range of users and environmental conditions. One or more of the following balanced features can allow valve 30 to function reliably, when employed with mask 100, to a pressure corresponding to a diving depth as low as 450 m.

Continuing to refer to FIGS. 4A-4C, valve 30 generally comprises the spring 320 or other resilient element to bias valve actuator 310 in its closed position (FIG. 4B) with respect to body 300. As described above, it can be a challenge to design a valve and/or breathing mask that consistently and accurately opens and closes in response to a user's respiration, for example, due to the low pressures provided by a user's inhalation and exhalation, and the various ranges of pressures in which the breathing mask might be used. Such challenges can arise with respect to the design and functionality of spring 320, which generally has a relatively low spring coefficient, to allow for actuation at low pressures inherent to exhalation, while still consistently holding valve 30 closed during inhalation. Providing balancing features to exhaust valve 30 can improve the actuation of valve 30, and as such, counter-balance the forces provided by spring 320. Valve 30 can also include various optional adjustment features to further fine-tune such balancing.

In some embodiments, the valve actuator 310 can comprise a balance inlet 316, a balance outlet 317, and an inner balancing channel 318 extending between the balance inlet 316 and the balance outlet 317. The balance outlet 317 can be in fluid communication with a balance chamber 341 within a pneumatic balancer 340. Balancer 340 can comprise a balance chamber portion 340A (which comprises the balance chamber 341) and an adjustment portion 340B, as described further below. Portions 340A and 340B can be separable from and/or movable with respect to each other, but are preferably fixed with respect to each other in one or more directions, such that balancer 340 is a "fixed balance" or "fixed balance chamber," as described below, and in contrast with a "floating balance" or "floating balance chamber." Portions 340A and 340B can be separately or integrally formed with respect to each other.

Balance chamber 341 can be positioned on the opposite side of spring 320 with respect to body exhaust 302. The balance inlet 316, outlet 317, channel 318, balancer 340 and balance chamber 341 can allow fluid communication between the body exhaust 302 to a position on the opposite side of spring 320, for example, when valve 30 is in a closed position. Such communication can provide a counterbalance in pressure or vacuum (e.g., a pneumatic balance) with respect to the force provided by spring 320.

For example, in an embodiment in which a vacuum is pulled on exhaust 302, the vacuum will create a vacuum bias on actuator 310 towards the closed position, in addition to any spring bias from spring 320. These biases can be balanced through an opposed or counterbalanced vacuum bias caused by a portion of the vacuum that flows to balance chamber 341 on the opposite side of spring 320. This opposed vacuum bias can allow valve 30 to be more easily activated by counteracting the combined spring bias of spring 320 and the vacuum bias from exhaust 302 on actuator 310.

Balancer 340 can be received by and positioned within valve body 300 (e.g., within valve body channel 303), and/or can be an integrally formed part of valve body 300. In some embodiments, balancer 340 can be sealed with respect to body channel 303, to prevent leakage therebetween, with a seal 342 comprising, for example, an o-ring 342A and groove 342B, similar to seals 305, 306, o-rings 305A, 306A, and grooves 305B, 306B, described elsewhere herein. In some embodiments, balancer 340 can provide a "fixed balance chamber" as described further below, and in contrast with, a "floating balance chamber" as described with respect to demand valve 20.

In some embodiments, the balancer 340 can be optionally movably engaged or adjustable with respect to the valve actuator body 311. Such adjustment of balancer 340 can adjust the spring force between actuator 310 and body 300, the volume of balance chamber 341, and/or the amount of flow allowed between seats 307 and 313 when valve 30 is opened. For example, balancer 340 can include threads 343 that allow it to be adjusted in the directions shown by arrows 501 and 502. Such adjustability can affect the amount of force required to overcome spring 320 and actuate valve 30 during a user's exhalation, to provide improved reliability during various uses and environmental conditions of mask 100. Generally, the pressure (or vacuum) of the exhaust flowing through valve 30 may not need to be significantly adjusted at various pressures (e.g., simulated depths in a hyperbaric chamber), and thus, balancer 340 can sometimes be set at a first point without additional adjustment during use at various pressures.

A seal 345 comprising an o-ring 345A and a groove 345B can be employed between balancer 340 and valve actuator 310, to prevent leakage between balance chamber 341 and channel 303. In some embodiments, an optional stop can be employed to prevent complete removal of balancer 340 from valve 30; for example, a captivating pin 344 can be employed to extend through corresponding apertures 314 in body 300, when balancer 340 is received therein.

Similar optional adjustability and sealing features can be provided to embodiments of body valve seat portion 307. For example, body valve seat portion 307 can include optional threads 309 that can provide adjustment of the spring force on actuator 310, the amount of flow between seats 307 and 313, and/or the volume of balance chamber 341, similar to that described above for threads 343. Adjustment of body valve seat portion 307 can also move the position of the point of sealing between seat 307 and seat 313 of valve actuator 310 with respect to body 300. Body valve seat portion 307 can also include a seal 319 comprising an o-ring 319A and a groove 319B with similar function as seal 342, o-ring 342A, and o-ring 342B.

Demand Valve 20

Figure 5A:
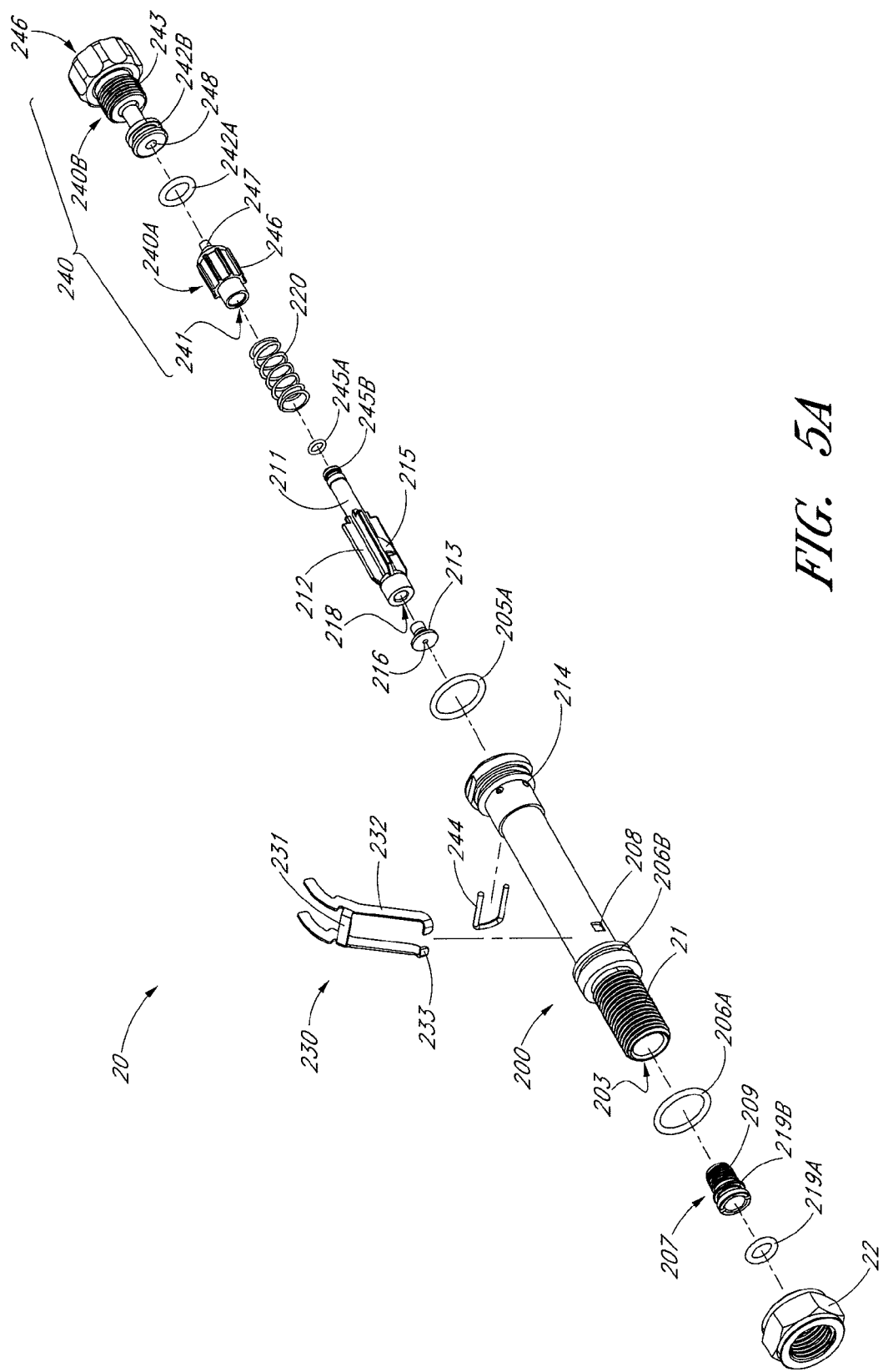
FIG. 5A is an exploded perspective view of an embodiment of a demand valve for a breathing mask.
Figure 6C:
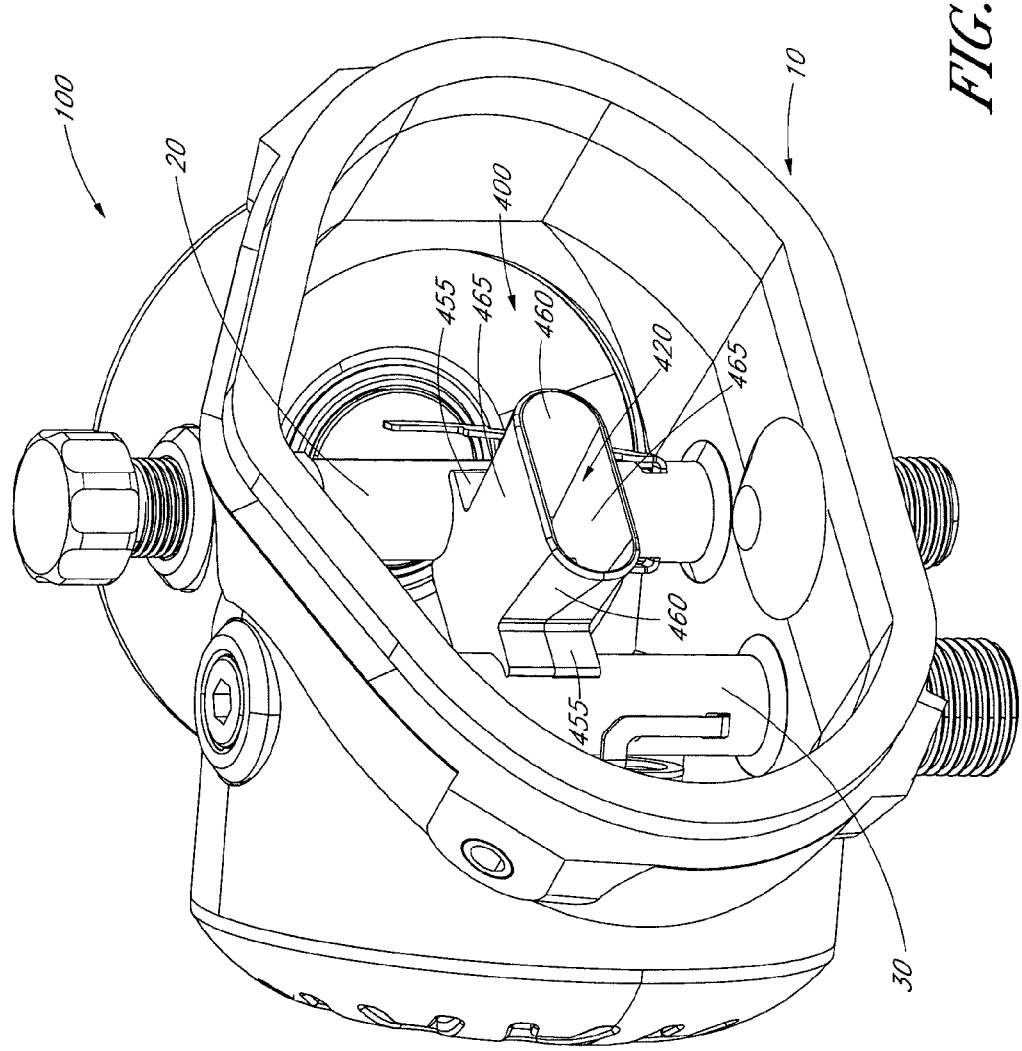
FIG. 6C is a rear perspective view of the diverter of FIG. 6A assembled with a breathing mask.

Referring to FIGS. 5A-5C, demand valve 20 can include many components that are substantially similar to those described herein with respect to exhaust valve 30 and shown in FIGS. 4A-4C. Such substantially similar components are shown in FIGS. 5A-5C numbered with a prefix "2" instead of "3." Thus, for example, demand valve 20 can include a valve body 200 and a valve actuator 210 that are substantially similar to valve body 300 and valve actuator 310 as described herein with respect to exhaust valve 30, and so forth, with one or more of the following differences.

Fluid can flow through demand valve 20 in a direction opposite to that of exhaust valve 30 with respect to a user's respiratory system. For example, the positioning of body inlet 201 and body outlet 202 of demand valve 20 can be reversed on body 200 with respect to the positioning of body inlet 301 and body outlet 302 of body 300 described herein.

Additionally, demand valve 20 can be configured to open in response to a user's inhalation, and to close in response to a user's exhalation. Referring to FIGS. 5B and 5C, actuator 210 can be linked to diaphragm 71 through an activation member, shown as lever 230, which can be moved by engagement element 73, through surface contact, and in some embodiments, without head or linkage 77 (FIGS. 4B; 4C).

When valve 20 is in an at-rest position, or when a user is exhaling, diaphragm 71 is held in the position shown in FIG. 5B. In such a position, lever 230 is engaged with actuator tabs 215 in a position such that actuator 210 and valve 20 are closed, restricting flow between seats 207 and 213, and between inlet 201 and outlet 202 through channel 203.

Referring to FIG. 5C, when a user inhales, pressure on diaphragm 71 causes it to move or flex outwardly, in the direction shown by arrows 504. In response, engagement element 73 (with or without head 77) can cause lever 230 to move, which in turn causes lever tabs 233 to engage with and move actuator tabs 215 (see also FIG. 5A). This in turn causes actuator 210 to move from a closed to an open position. Once valve 20 opens, fluid can flow through inlet 201 (arrow 508; FIG. 5C), through channel 203, between seats 207 and 213 (arrows 509), and out the exhaust 302 (arrow 510). Upon a user's subsequent exhalation, the valve 20 will return to the closed configuration shown in FIG. 5B, with the diaphragm 71 moving outwardly to the closed position, as indicated by arrow 503.

Valve 20 can include substantially similar adjustment and balancing functionality and components as described above for valve 30. One difference is that a positive pressure fluid is generally supplied to inlet 201, and thus the bias to keep valve 30 closed is provided by spring 220 and the counterbalance of pressure within balance chamber 241. This is different from the function described above for valve 30, where the exhaust vacuum and spring can have a combined bias towards closing valve 30, and the counterbalance of vacuum provides a bias towards opening valve 30.

Fixed vs Floating Balance

Another difference is that balancer 240 can comprise a floating balance chamber portion 240A (which comprises a floating chamber 241) and a balancer adjustment portion 240B. Portions 240A and 240B can be separable from and/or movable with respect to each other. Such functionality can be beneficial for demand valve 20, because demand valve 20 may be adjusted regularly during use. For example, a user of mask 100 may adjust the pressure of a fluid supply to valve 20 to correspond various diving depths. To compensate for such pressure variations, adjustment portion 240B may be adjusted, to adjust the spring force on spring 220, so that valve 20 will continue to reliably open and close under such pressure variations. However, such adjustment (e.g., rotation) of adjustment portion 240A can increase wear between floating chamber portion 240A, spring 220, and/or seal 245. Thus, floating chamber portion 240A can be movable with respect to adjustment portion 240B, such that floating chamber portion 240A does not substantially move with respect to spring 220 and seal 245 during adjustment of portion 240B.

Referring again to FIGS. 4A-4C, the aforementioned continuous adjustment of pressure or vacuum may not be required on the vacuum supply (or exhaust line) extending from valve 30. Thus, in some embodiments, as described above, balancer 340 can be configured such that balance chamber portion 340A (and thus balance chamber 341), and adjustment portion 340B are fixed in at least one direction with respect to each other, such that balancer 340 is a "fixed balance" or "fixed balance chamber." For example, balance chamber 341 may be fixed longitudinally with respect to adjustment portion 340B, to prevent chamber 341 from move downwardly against spring 320 once vacuum was applied to balance chamber 341. Balance chamber 341 may also be fixed rotationally with respect to adjustment portion 340B, although it will be understood that portions 340A and 340B can be fixed longitudinally, while still allowing for rotational movement therebetween, using a captured rotational element or other known structure. A valve with the aforementioned "fixed balance chamber" or "fixed balance" may be initially adjusted (through rotation of adjustment portion 340B using threads 343) to set the cracking pressure of valve 30 (with respect to the pressure or vacuum in the exhaust line), without additional significant adjustment once the valve is in use.

Diverter

It can be beneficial to control or channel the flowpath of fluid within a breathing mask. For example, fluid entering or exiting the supply and exhaust valves can cause turbulence within the inner volume of a mask. Such turbulence can interfere with the activation elements, such as the diaphragm assemblies, that control the opening and closing of the valves, decreasing the reliability of the valve function. Additionally, stagnant zones or "dead pockets" can form within the mask in areas with reduced circulation, causing buildup of residual carbon dioxide from a user's previous exhalation, or buildup of unused inhalation fluid that could otherwise be inhaled. The following discloses embodiments of a fluid router or diverter that can be employed within a breathing mask, to provide improved reliability of the demand and/or exhaust valves, and/or to provide improved fluid flow and efficiency within the mask. It will be understood that while the embodiments of the fluid diverter described herein are illustrated with reference to mask 100, the invention should not be limited as such, and can be employed with other breathing masks known or described herein.

FIGS. 6A-7B show embodiments of a router or diverter 400 that can be employed within a breathing mask, such as breathing mask 100. Diverter 400 can comprise a tubular diverter body 410 comprising a breathing port 420 configured to fluidly communicate with a user's respiratory system. An inner breathing channel 415 can extend from breathing port 420 into diverter body 410. Diverter 400 can include an exhaust port 425 configured to engage the tubular diverter body 410 with a breathing mask exhaust valve, such as exhaust valve 30 (see FIG. 6C). Diverter 400 can further include a demand port 430 configured to engage the tubular diverter body 410 with a breathing mask demand valve, such as demand valve 20.

Diverter body 410 is not limited to a particular cross-sectional shape, and can comprise any of a number of suitable regular or irregular cross-sectional shapes with a hollow portion that will form channel 415 when extended longitudinally, such as a square, rectangle, parallelogram, ellipse, circular, or other shape. Likewise, channel 415 is not limited to any particular shape, and can comprise any suitable shape for channeling fluid, and can include substantially parallel or non-parallel sides, and/or substantially planar or non-planar surfaces, and/or can transition between one or more cross-sectional shapes along its longitudinal length. In some embodiments, body 410 can comprise two or more walls that converge or diverge to channel flow or adjust fluid velocity within diverter 400. In the illustrated embodiment, body 410 comprises a pair of opposed diverging walls 460 that diverge from breathing port 420 towards demand and exhaust ports 425, 430, so as to improve fluid flow towards exhaust port 425, and away from demand port 430. Body 410 is illustrated with a second pair of substantially parallel opposed walls 465; however it will be understood that any of walls 460 and 465 can be opposed, non-opposed, diverging, non-diverging, and substantially parallel or non-parallel.

The demand and exhaust ports 425, 430 can be configured in any way suitable to engage with a corresponding demand and exhaust valve, when diverter 400 is employed with a breathing mask. Ports 425, 430 can engage with a valve using any of a number of engagement elements known or described herein, such as tabs 450 which facilitate removable engagement with a corresponding port on a corresponding breathing mask valve. In some embodiments, ports 425, 430 can sufficiently engage with a breathing mask valve, to provide a seal, to reduce leakage between ports 425, 430 and a corresponding port on breathing mask valve. Ports 425, 430 can be positioned along various portions of body 410; in the illustrated embodiment, ports 425, 430 are positioned along walls 460. In some embodiments, ports 425 and 430 can be positioned on approximately opposed sides (e.g., lateral sides) of body 410.

In some embodiments, ports 425, 430 can include structure to more closely conform to the shape of a port on a breathing mask. For example, an optional flange, lip or other suitable structure, such as flange portions 455, can extend from body 410 so as to improve such conformance between ports 425, 430 and a breathing mask valve port (see FIGS. 6C-7B).

A dividing wall or diverter wall 435 can extend within the tubular diverter body 410 so as to divide at least a portion of the breathing channel 415 into an exhaust channel 416 and a demand channel 417. The diverter wall 435 can provide a barrier between the exhaust port 425 and the demand port 430, so as to prevent the direct flow of fluid between the exhaust port and the demand port, and reduce turbulence during use of diverter 400 with a breathing mask.

The diverter wall 435 can extend within body 410 along a portion of some, most, or substantially the entirety of breathing channel 415. In some embodiments, the diverter wall 435 can extend beyond a perimeter of body 410 and opening 420, so as to channel fluid flow into breathing channel 415 and exhaust channel 416 even prior to the fluid entering body 410. In the illustrated embodiment, and referring to FIG. 6B, a leading edge 436 of the diverter wall can be positioned closer to the breathing port 420 than a plane 520 extending between a leading edge of the inlet port and a leading edge of the exhaust port. Such an embodiment can reduce the likelihood that fluid will flow from one of the exhaust port 425 and demand port 430, and around diverter wall 435 to the other of the exhaust port 425 and demand port 430. Such embodiments may reduce turbulence, dead spots, and reliability issues on the mask demand and exhaust valves when diverter 400 is employed within a breathing mask.

In some embodiments, a second diverter wall 445 can be configured to extend within the diverter body 410 from the first diverter wall 435 to the inlet port 430. Such an embodiment can form a flowpath that extends from the demand port 430, along the second diverter wall 445, from the second diverter wall 445 towards and along the first diverter wall 435, and from the first diverter wall 435, into breathing channel 415, and towards and through the breathing port 420. This flowpath can channel breathing fluid from a breathing mask demand valve, and towards a user of diverter 400 within a breathing mask, during user inhalation, reducing unused breathing fluid, and increasing the mask's efficiency. Second diverter wall 445 can further improve a mask's reliability, by isolating the fluid flowing from the demand valve from the diaphragms, to prevent unwanted activation of the exhaust valve. In some embodiments, the first and second diverter walls 435, 445, and the demand port 430 are configured such that a portion of the flowpath extending within the exhaust channel is unbroken, i.e., without additional intervening structure or ports that might reduce flow fluid therethrough (see FIG. 7A).

In some embodiments, diverter 400 can include a purge port 440 in fluid communication with the exhaust channel 416. Such embodiments can allow fluid to be exhausted from the breathing port 420 and the purge port 440 through the exhaust port 425. Such embodiments can, for example, reduce stagnant zones or dead spots within a mask 100 in which diverter 400 is employed, such as those dead zones of carbon dioxide that may form between the valves 20, 30 and the front portion of mask 100 (see FIG. 7B). The purge port 420 can extend through various portions of body 410 suitable to provide fluid communication with exhaust channel 416, such as, for example, a portion of upper wall 465 (FIG. 6A). In the illustrated embodiment, purge port 440 extends through an anterior portion of body 410. In some embodiments, the purge port 440 and the breathing port 420 are positioned on opposed portions of the diverter body.

Although illustrated within various contexts, embodiments of the present invention may also be used in other applications. For example, the diverter and breathing mask valves described herein may be employed with other types of breathing masks than those for a hyperbaric chamber. Additionally, the embodiments of the mask, various mask components, valves, and/or diverter described herein can be configured separately, or as an assembly or kit in any of a number of combinations. For example, the diverter and/or valve can be configured separately from each other and the remainder of the mask, or can be combined or assembled as part of the mask, and the mask can be configured without some components, such as the diverter. It will be understood by those of skill in the art that additional numerous and various modifications can be made without departing from the spirit of the present invention. Therefore, it should be clearly understood that the forms of the invention described herein are illustrative only and are not intended to limit the scope of the invention.

What is claimed is:

1. A breathing mask for a hyperbaric chamber comprising:
   a housing configured to form an inner volume, the housing comprising:
      an inlet configured to allow fluid flow into the inner volume;
      an exhaust configured to allow fluid flow from the inner volume;
      a posterior opening configured to provide fluid communication between the inner volume and a user's respiratory system; and
      first and second anterior openings extending through an anterior portion of the housing;
   a pneumatically-balanced exhaust valve configured to selectively flow fluid between the exhaust and the inner volume;
   a pneumatically-balanced demand valve configured to selectively flow fluid between the inlet and the inner volume, wherein each of the exhaust valve and the demand valve is configured to have a first bias, and wherein each valve is configured to pneumatically provide a second bias configured to reduce the amount of the first bias;
   a first diaphragm covering the first anterior opening; and
   a second diaphragm covering the second anterior opening, wherein the first and second diaphragms are configured to move in response to a change in pressure within the inner volume during inhalation and exhalation by a user;
   wherein the first diaphragm is mechanically linked to the exhaust valve such that the exhaust valve opens and closes in response to movement of the first diaphragm, and wherein the second diaphragm is mechanically linked to the demand valve such that the demand valve opens and closes in response to movement of the second diaphragm.

2. The breathing mask of claim 1, wherein the housing further comprises a first aperture and a second aperture spaced from the inlet and the exhaust, wherein a portion of the demand valve and the exhaust valve, respectively, can be secured to the first and the second aperture.

3. The breathing mask of claim 2, wherein the first and second apertures are positioned on a first portion of the housing, and the inlet and the exhaust are positioned on a second, opposing portion of the housing, wherein the demand valve extends across the inner volume between the first aperture and the inlet, and the exhaust valve extends across the inner volume between the second aperture and the exhaust.

4. The breathing mask of claim 2, wherein the demand valve, the exhaust valve, the first and second aperture, the inlet, and the exhaust are configured such that the demand valve and the exhaust valve can be inserted into the housing through the first and second aperture, respectively, in a first direction, without disassembly of the demand valve and the exhaust valve.

5. The breathing mask of claim 1, wherein the housing comprises a pair of laterally-diverging portions through which the first and second anterior openings extend.

6. The breathing mask of claim 1, wherein the exhaust valve comprises a fixed balance chamber.

7. The breathing mask of claim 1, wherein the demand valve comprises a floating balance chamber.

8. The breathing mask of claim 1, further comprising a spring, wherein at least a portion of the first bias on the exhaust valve is provided by the spring.

9. The breathing mask of claim 8, wherein at least a portion of the first bias on the exhaust valve is provided by a vacuum connected to the exhaust.

10. A breathing mask comprising:
    a body comprising an inlet and an exhaust;
    a respiratory interface configured to provide fluid communication between each of the inlet and the exhaust, and a user's respiratory system;
    a pneumatically balanced exhaust valve configured to selectively flow fluid between the exhaust and the respiratory interface wherein the exhaust valve is configured to have a first bias, and wherein the exhaust valve is pneumatically connected to the exhaust so as to pneumatically provide a second bias configured to reduce the amount of the first bias; and
    an inlet valve configured to selectively flow fluid between the inlet and the respiratory interface.

11. The breathing mask of claim 10, wherein the exhaust valve comprises a fixed balance chamber.

12. The breathing mask of claim 10, wherein the inlet valve comprises a balanced inlet valve comprising a floating balance chamber.

13. The breathing mask of claim 10, wherein the body further comprises an aperture spaced from the exhaust, wherein a portion of the exhaust valve can be secured to the aperture.

14. The breathing mask of claim 13, wherein the aperture is positioned on a first portion of the housing, and the exhaust is positioned on a second, opposing portion of the housing, wherein the exhaust valve extends across an inner volume within the body between the second aperture and the exhaust.

15. The breathing mask of claim 14, wherein the exhaust valve, the aperture, and the exhaust are configured such that the exhaust valve can be inserted into and removed from the body through the aperture, without disassembly of the exhaust valve.

16. The breathing mask of claim 10, further comprising a first and second diaphragm linked to the exhaust valve and inlet valve, such that the exhaust valve opens and closes in response to movement of the first diaphragm, and such that the inlet valve opens and closes in response to movement of the second diaphragm, wherein the first and second diaphragms, the demand valve, and the exhaust valve are substantially entirely enclosed within a perimeter of the body.

17. A pneumatically-balanced exhaust valve, comprising:
    a valve body comprising a body inlet, a body exhaust, and a body channel extending between the body inlet and the body exhaust;
    a valve actuator positioned within the body channel and configured to be movable with respect to the valve body between an open and a closed position, so as to selectively allow and restrict fluid flow between the body inlet and the body exhaust, wherein the valve actuator comprises:
       a balance inlet;
       a balance outlet; and
       an inner balancing channel extending between the balance inlet and the balance outlet; and
    a pneumatic balancer comprising a balance chamber in fluid communication with the balance outlet, the balancer movably engaged with respect to the valve actuator body.

18. The pneumatically-balanced exhaust valve of claim 17, wherein the balance chamber comprises a fixed balance chamber.

19. The pneumatically-balanced exhaust valve of claim 18, wherein the balancer comprises a balance chamber portion and an adjustment portion, wherein the balance chamber portion comprises the balance chamber, and the balance chamber portion is substantially fixed in at least one direction with respect to the adjustment portion, and wherein the adjustment portion is configured so as to allow the movable engagement with respect to the valve actuator body.

20. The pneumatically-balanced exhaust valve of claim 19, wherein the balance chamber portion is substantially fixed in a longitudinal direction with respect to the adjustment portion.

21. The pneumatically-balanced exhaust valve of claim 19, wherein the balance chamber portion and the adjustment portion comprise an integrally formed piece.

22. A breathing mask diverter, comprising:
a tubular diverter body comprising an inner breathing channel;
a breathing port configured to provide fluid communication between the inner breathing channel and a user's respiratory system;
an exhaust port configured to engage the tubular diverter body with a breathing mask exhaust valve;
a demand port configured to engage the tubular diverter body with a breathing mask demand valve; and
a diverter wall extending within the tubular diverter body, wherein the diverter wall divides at least a portion of the breathing channel into a separate exhaust channel and a separate demand channel, and wherein the diverter wall provides a barrier between the exhaust port and the demand port, so as to prevent the direct flow of fluid between the exhaust port and the demand port.

23. The breathing mask diverter of claim 22, wherein the demand port and the exhaust port are positioned on approximately opposed lateral sides of the diverter body.

24. The breathing mask diverter of claim 22, wherein the diverter body comprises at least a pair of diverging walls configured to direct fluid from the breathing port towards the exhaust channel and the demand channel.

25. The breathing mask diverter of claim 22, wherein at least one of the exhaust port and the demand port comprise one or more tabs configured to removably engage with a corresponding port on the breathing mask exhaust or demand valve.

26. The breathing mask diverter of claim 22, wherein the diverter wall comprises a first diverter wall, further comprising a second diverter wall extending within the diverter body from the first diverter wall to the inlet port, so as to form a flowpath that extends from the demand port and along the second diverter wall, from the second diverter wall towards and along the first diverter wall, and from the first diverter wall, towards and through the breathing port.

27. The breathing mask diverter of claim 26, wherein the first and second diverter walls and the demand port are configured such that a portion of the flowpath extending within the exhaust channel is unbroken.

28. The breathing mask diverter of claim 22, further comprising a purge port in fluid communication with the exhaust channel, so as to allow fluid to be exhausted from the breathing port and the purge port through the exhaust port.

29. The breathing mask diverter of claim 28, wherein the purge port and the breathing port are positioned on opposed portions of the diverter body.

30. The breathing mask diverter of claim 22, in further combination with a breathing mask, a breathing mask exhaust valve, and a breathing mask demand valve.

* * * * *

UNITED STATES PATENT AND TRADEMARK OFFICE
CERTIFICATE OF CORRECTION

PATENT NO. : 8,336,547 B1
APPLICATION NO. : 13/354597
DATED : December 25, 2012
INVENTOR(S) : Ritchie et al.

Page 1 of 1

It is certified that error appears in the above-identified patent and that said Letters Patent is hereby corrected as shown below:

In the Specification

Column 8, Line 29, After "20," insert --30--.

Signed and Sealed this
Twenty-fourth Day of September, 2013

Teresa Stanek Rea
*Deputy Director of the United States Patent and Trademark Office*